United States Patent
Hillesheim et al.

(10) Patent No.: US 9,200,092 B2
(45) Date of Patent: Dec. 1, 2015

(54) $\eta^5$:$\eta^1$-CYCLOPENTADIENYLIDENE-PHOSPHORANE CONSTRAINED GEOMETRY COMPLEXES OF RARE EARTH METALS

(75) Inventors: Nina Hillesheim, Marburg (DE); Jörg Sundermeyer, Marburg (DE)

(73) Assignee: Rockwood Lithium GmbH, Frankfurt am Main (DE)

( * ) Notice: Subject to any disclaimer, the term of this patent is extended or adjusted under 35 U.S.C. 154(b) by 0 days.

(21) Appl. No.: 14/235,259

(22) PCT Filed: Aug. 2, 2012

(86) PCT No.: PCT/EP2012/003292
§ 371 (c)(1),
(2), (4) Date: Jan. 27, 2014

(87) PCT Pub. No.: WO2013/017280
PCT Pub. Date: Feb. 7, 2013

(65) Prior Publication Data
US 2014/0163187 A1    Jun. 12, 2014

(30) Foreign Application Priority Data
Aug. 2, 2011  (DE) .......................... 10 2011 080 283

(51) Int. Cl.
| | | |
|---|---|---|
| *C07F 17/00* | (2006.01) | |
| *C07F 9/54* | (2006.01) | |
| *C08F 4/52* | (2006.01) | |
| *C08F 10/00* | (2006.01) | |
| *B01J 31/02* | (2006.01) | |
| *B01J 31/22* | (2006.01) | |
| *C07F 9/535* | (2006.01) | |
| *C08F 36/08* | (2006.01) | |
| *C08G 63/84* | (2006.01) | |
| *C08G 63/82* | (2006.01) | |

(52) U.S. Cl.
CPC .............. *C08F 4/52* (2013.01); *B01J 31/0235* (2013.01); *B01J 31/2265* (2013.01); *B01J 31/2295* (2013.01); *C07F 9/5352* (2013.01); *C07F 9/54* (2013.01); *C07F 17/00* (2013.01); *C08F 36/08* (2013.01); *C08G 63/823* (2013.01); *C08G 63/84* (2013.01); *B01J 2531/0205* (2013.01); *B01J 2531/36* (2013.01); *B01J 2531/37* (2013.01); *B01J 2531/38* (2013.01)

(58) Field of Classification Search
CPC ............ C07F 17/00; C07F 17/05; C07F 9/28; C07F 9/54; C08F 4/52; C08F 10/00
See application file for complete search history.

(56) References Cited

U.S. PATENT DOCUMENTS

| | | |
|---|---|---|
| 5,703,187 A | 12/1997 | Timmers |
| 6,013,819 A | 1/2000 | Stevens et al. |
| 6,670,432 B1 | 12/2003 | Timmers |

(Continued)

FOREIGN PATENT DOCUMENTS

| | | |
|---|---|---|
| DE | 10 2007 057 854 A1 | 6/2009 |
| EP | 0 416 815 A2 | 3/1991 |

OTHER PUBLICATIONS

Hillesheim, N. S. "Poster Contributions", 7th International Conference of I Elements, ICFE, Aug. 23-27, 2009.

(Continued)

*Primary Examiner* — Caixia Lu
(74) *Attorney, Agent, or Firm* — Norton Rose Fulbright US LLP

(57) ABSTRACT

The invention relates to $\eta^5$:$\eta^1$-cyclopentadienylidene-phosphorane constrained geometry complexes of rare earth metals, abbreviated to $\eta^5$:$\eta^1$-CpPC-CGC, method for production and use of same. The $\eta^5$:$\eta^1$-CpPC-CGCs correspond to the general formula (1), wherein SE=Sc, Y, La, Ce, Pr, Nd, Pm, Sm, Eu, Gd, Tb, Dy, Ho, Er, Tm, Yb or Lu; X=independently of one another, a mono-anionic diorganoamido-, bistrimethylsilylamido-, halogenido-, alkyl-, aryl-, alkoxo-, aryloxo- or alkylaluminate ($AlR_4^-$) substituent; L=neutral ligand ($PR_3$, $NR_3$, pyridine), solvent molecule (THF, ether, DMF, DMSO, HMPT, tetrahydropyran THP, tetrahydrothiofuran THT); R=alkyl with up to 1-10 C atoms or mono- or polycyclical aryl with 6 to 20 C atoms; $R^1$, $R^4$=independently of one another H or methyl; $R^2$, $R^3$=independently of one another, H or methyl or tertiary butyl or together a substituted cycloalkyl group; $R^5$, $R^6$=methyl, n-butyl, tertiary butyl or phenyl; $R^7$, $R^8$=independently of one another H, trimethylsilyl, alkyl with 1-10 C atoms or mono- or polycyclical aryl with 6 to 20 C atoms, and m=0, 1, 2 or 3.

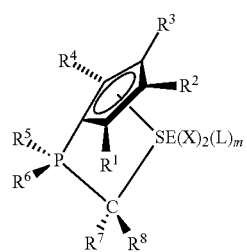

(1)

25 Claims, 4 Drawing Sheets

(56) References Cited

U.S. PATENT DOCUMENTS

| | | |
|---|---|---|
| 6,806,326 B2 | 10/2004 | Stevens et al. |
| 6,858,557 B1 | 2/2005 | Stevens |
| 6,884,857 B1 | 4/2005 | Stevens et al. |
| 2011/0034715 A1 | 2/2011 | Sundermeyer et al. |

OTHER PUBLICATIONS

Kotov, et al. "Alkylaminophosphanyl substituted half-sandwich complexes of vanadium(III) and chromium(III): preparation and reactivity in ethylene polymerisation", J. of Organometallic Chem., 640 (2001), pp. 21-28.

Kotov, et al. "Alkyl(annino)- and Alkyl(chloro)phosphanyl-Substituted Cyclopentadienyl Complexes of Titanium and Zirconium", Eur. J. Inorg. Chem. (2002), pp. 678-691.

Panda, et al. "Rare Earth and Alkalyne Earth Metal Complexes with Me2Si-Bridged Cyclopentadienyl-Imidazolin-2-Imine Ligands and Their Use as Constrained-Geometry Hydroamination Catalysts", Eur. J. Inorg. Chem. (2008), pp. 4270-4279.

Petrov, et al. "P-amino-cyclopentadienylidene-phosphoranes versus P-cyclopentadienyl-iminophosphoranes—tautomeric protic forms of a bew bidentate CpPN ;igand system", Dalton Trans., (2008), pp. 909-915.

Ramirez, et al. "A New Type of Azo Compound by Coupling at the Cyclopentadienide Ring", J. Org. Chem., 21, 488, (1956), p. 1333.

Randoll, et al. "Chromium Complexes with Me2Si-Bridged Cyclopentadienyl-imidazolin-2-imine Ligands: Synthesis, Structure, and Use in Ethylene Polymerization Catalysis", Organometallics, 27 (2008), pp. 3232-3239.

Rufanov, et al. "Synthesis of (Indenylidene)phophoranes—A Novel Class of Ligand Precursors for Main-Group and Transition Metal Organometallics", Eur. J. Inorg. Chem. (2004), pp. 4759-4763.

Rufanov, et al. "A Lutetium Cyclopentadienyl-Phosphazene Constrained Geometry Complex (CGC): First Isolobal Analogues of Group 4 Cyclopentadienyl-Silylamido CGC Systems", Eur. J. Inorg. Chem. (2005), pp. 3805-3807.

Schmidbaur, Hubert "Phosphorusw Ylides in the Coordination Sphere of Transition Metals: An Inventory" Angew. Chem. Int. Ed. Engl. 22 (1983), pp. 907-927.

Shapiro, et al. "[. . . ]A Unique Example of a Single-Component a-Olefin Polymerization Catalyst", Organometallics 9, (1990), pp. 867-869.

Schumann, et al. "Lanthanide(III)-tris(dimethylphosphonium-bismethylide)", Chemiker-Zeitung, 100 (1976), p. 336 [With English translation].

Schumann, et al. "Organometallic compounds of lanthanoids. XIV. Lutetium complexes of di-t-butyl phosphonium-bis-(methylide)", Journal of Organometallic Chemistry, 235 (1982), pp. 287-294 [With English translation].

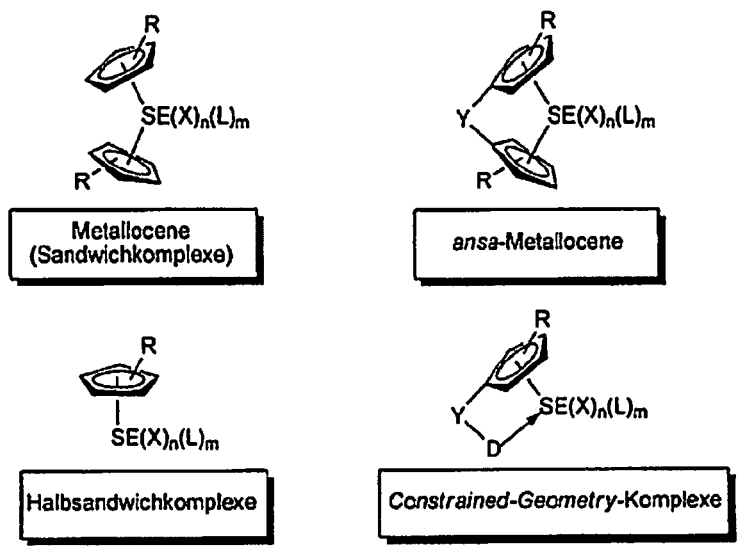
Figure 1 Monodentate Cp ligands (left); bidentate *ansa*-Cp ligands (right) in complexes of rare earth metals
[Glossary: Metallocene (Sandwichkomplexe) = metallocenes (sandwich complexes); *ansa*-Metallocene = *ansa*-metallocene; Halbsandwichkomplexe = half-sandwichs complexes]

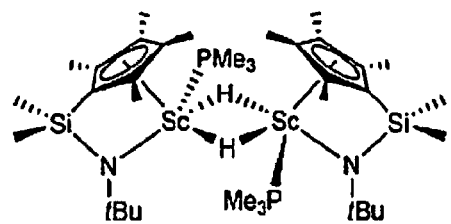
Figure 2: The first published CGC complex with a CpSiN ligand motif by BERCAW.
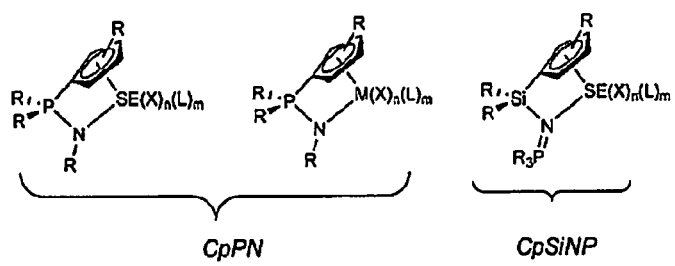
Figure 3: *Cp*Y-D complexes of rare earth metals and of the metals metals M (M = Ti, Zr, Hf, Al, V, Cr; X = alkyl, benzyl, amido, halogenide)
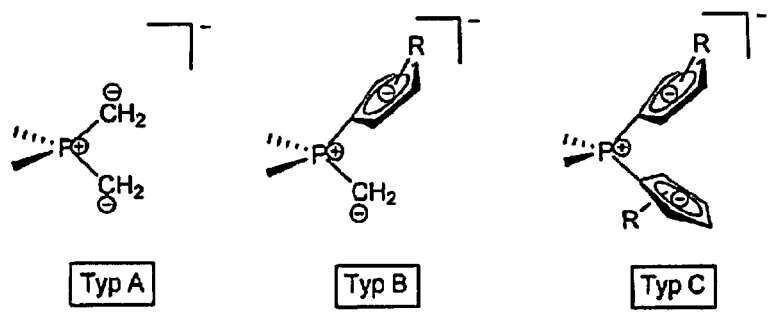
Figure 4: Analogues of the novel mono-Cp-substituted phosphonium diylide type B in relation to previously known bis-Cp-substituted type A and of the classic type C

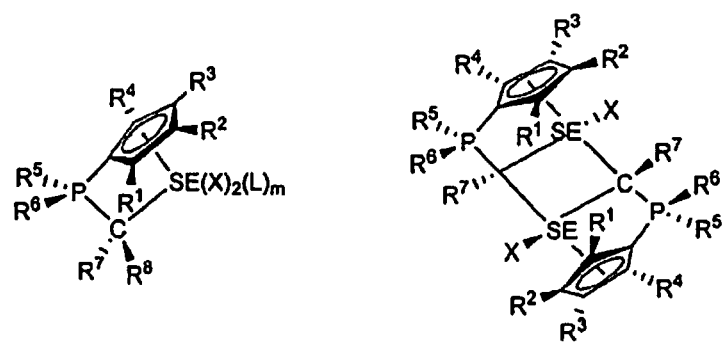
Figure 5: Novel RE complexes with: a) monoanionic and b) dianionic CpPC ligand

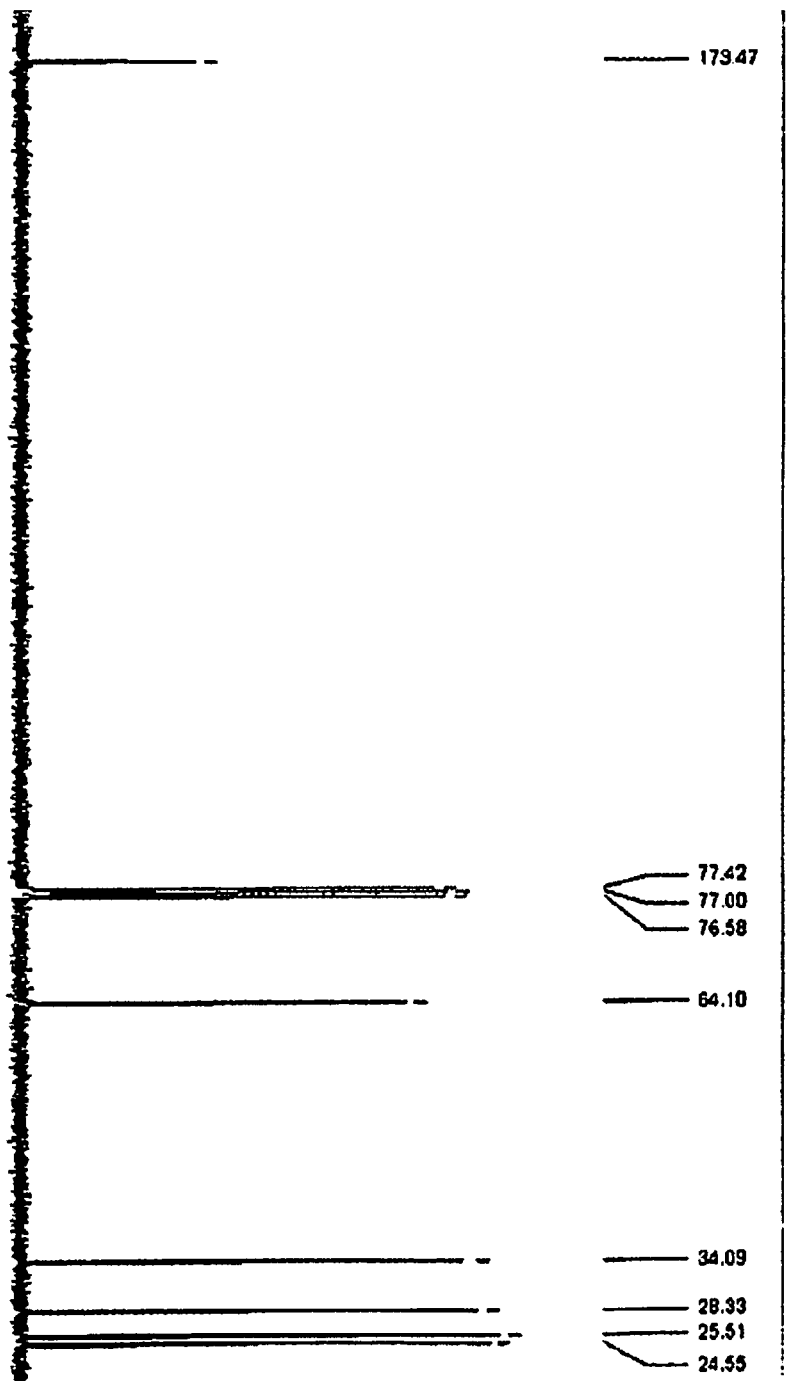
Figure 6: $^{13}$C-NMR spectrum of polycaprolactone, polymerized by $\eta^5:\eta^1$-C$_5$Me$_4$PMe$_2$CH$_2$)La(N(SiMe$_3$)$_2$)$_2$],

$\eta^5{:}\eta^1$-CYCLOPENTADIENYLIDENE-PHOSPHORANE CONSTRAINED GEOMETRY COMPLEXES OF RARE EARTH METALS This application is a §371 of International Application No. PCT/EP2012/003292 filed Aug. 2, 2012, and claims priority from German Patent Application No. 10 2011 080 283.5 filed Aug. 2, 2011.

FIELD OF THE INVENTION

The invention relates to $\eta^5{:}\eta^1$-cyclopentadienylidene-phosphorane constrained geometry complexes of rare earth metals, abbreviated $\eta^5{:}\eta^1$-CpPC,-CGC, a method for their production and use.

BACKGROUND OF THE INVENTION

With the discovery of ferrocene in 1951, the cyclopentadienyl ligand (Cp) gained prominent renown in the field of organometallic chemistry of transition metals and advanced rapidly to dominate in form of bis(cyclopentadienyl) or metallocene complexes the metals of the d-block and p-block. With the development of tris-(cyclopentadienide) of the lanthanoids and of group 3 by WILKINSON and BIRMINGHAM, this ligand ultimately also achieved a successful breakthrough in the field of organometallic chemistry of rare earth metals (RE) that is highly sensitive to hydrolysis; syntheses of different bis-(cyclopentadienyl) derivatives followed thereafter.

The term metallocene, as it became known due to ferrocene, is used not only for pure bis-(cyclopentadienyl) complexes but also for complexes with metals that carry further anionic ligands (X) or neutral ligands (L) in form of $Cp^R{}_2RE(X)_n(L)_m$ (FIG. 1). $Cp^R{}_2RE(+II)$ and $Cp^R{}_2RE(+III)$ halogenides are excellent starting compounds for alkyl, hydrido or amido species. These in turn possess, ultimately, a reactive function for catalytic applications, primarily in hydrometalation reactions, cyclization reactions and polymerization reactions of olefins. Electronic or steric parameters can be varied by organyl substituents R on the cyclopentadienyl unit. Especially prominent variants of $C_5H_5$ are pentamethylcyclopentadienyl $C_5Me_4$, indenyl and fluorenyl units (in general, $Cp^R$).

A bridging Y (in most cases, $SiR_2$, —$C_nH_{2n}$—) of both $Cp^R$ units results in ansa-metallocenes. The conformation of the complex becomes fixed, whereby the LEWIS acidity of the metal center is successfully increased, because the catalyst center is rendered more accessible for larger substrate molecules in the catalysis. Correspondingly, the activity of the ansa-lanthanocene catalyst $\{Me_2Si(C_5Me_4)_2RE(H)\}_2$ is ten times higher in comparison to the unbridged lanthanocene $\{Cp_2RE(H)\}_2$ in the ethylene polymerization as well as in the copolymerization of ethane with 1-hexene.

Achiral ansa-metallocenes of the $Me_2Si(C_5Me_4)_2LnR$ and $Me_2Si(C_5Me_4)(C_5H_4)LnR$ types and chiral ansa-metallocenes were prepared in a broad variety. Chiral ansa-lanthanocenes play are crucially important in asymmetrical hydroamination, as described for the first time by MARKS shortly after the development of the highly efficient intramolecular hydroamination by achiral lanthanocenes.

The successful use of ansa-metallocenes in polymerization catalysis has intensified the interest in further reducing the steric requirements and in studying pure half-sandwich complexes with one or two reactive functions $CpRE^{II}(X)$ or $CpRE^{III}(X)_2$, respectively. Since the literature contains relatively little information regarding mono-Cp- as opposed to bis-Cp-systems, it is already obvious that the synthesis of such species is associated with difficulties. In particular, when a sterically undemanding Cp-moiety is to be inserted, in the ligand substitution, there ensues time and time again the formation of thermodynamically favored metallocene or tris-Cp complexes.

In addition, the more electropositive nature of the RE central atom results in a stronger ionic bond, which means the compound tends to undergo ligand substitution reactions (ligand scrambling). Although most neutral half-sandwich complexes do not show any activity in the polymerization of olefins, a transfer, however, by way of, for example, MAO or boranes, such as $[B(C_6F_5)_3]$, or borates, such as $[Ph_3C][B(C_6F_5)_4]$ or $[Ph_2MeNH][B(C_6F_5)_4]$, respectively, to a cationic active species resulted multiple times in the successful use in the context of regio- and stereospecific polymerizations of olefins, or also in copolymerization reactions with cyclic and aromatic monomers.

A more successful improvement resulted from the substitution of a cyclopentadienyl moiety in an ansa-metallocene with another anionic or neutral donor D obtaining the so-called constrained geometry complexes. Contrary to Cp-rings, which, by way of being inert, strongly protective ligands (spectator ligands), serve for the complex formation of a reactive metal center, the donor D has a more faceted function: it can be hemilabile during catalysis and be subject to temporary decomplexation without degradation of the catalyst system, or it can flexibly contribute 2, 4 or 6 electrons in $\alpha$- and $\pi$-bonds to the central atom.

BERCAW presented the first constrained geometry complex with the Cp-Y-D-ligand motif in 1990 (P. J. Shapiro, E. Bunel, W. Schaefer, J. E. Bercaw, *Organometallics* 1990, 9, 867-869) in form of a dimeric Sc-hydrido complex with the chelate unit CpSiN (FIG. 2).

Aside from the many prominent group 4 compounds, ansa-cyclopentadienyl complexes with rare earth metals form a class of interesting homogeneous catalysts that are also used on an industrial scale (EP 0416815A2).

Some novel structural motifs for constrained geometry complexes have been developed previously by Sundermeyer et al. They contain a chelating iminophosphorane unit with a strongly basic nitrogen atom (FIG. 3). Initially, based on the isoelectronic relationship of the dianionic unit CpSiN of the classic CGC relative to the monoanionic unit CpPN, a new series of ligands of different steric requirements and electronic donor nature was prepared. The first lutetium complex of the new system was published in 2005. I was possible to study a series of CpPN complexes of further rare earth metals and metals of the groups 3 and 4, where the CpPN unit functions as a chelate ligand, as well as the activity thereof in intramolecular hydroamination and in olefin polymerization (WO2009068000). Moreover, experiments were conducted regarding the synthesis of group 4, aluminum, chromium, vanadium and further rare earth metal CG complexes. Independently but simultaneously in relation to the above, BOURISSOU et al. published DFT calculations and experimental works regarding fluorenyl-based FluPN ligand systems and the complex formation thereof on group 4 metals.

As mentioned previously, in CpPN complexes, the phosphacene unit is bonded directly to the C5-ring via the phosphor atom and is therefore a component of the structurally verifiable chelate unit. The monoanionic CpSiNP ligand is a hybrid of the novel monoanionic CpPN and the classic dianionic CpSiN ligands, where the phosphacene unit is exocyclically arranged relative to C5-Si—N chelate ring that is the identified target. Also related to the ligand system that was described for the first time in 2010 are such compounds with $Me_2Si$-bridged cyclopentadienyl-imidazolin-2-imine ligands the N-atoms of which are also a component of an extremely basic, ampholyte-ionically constructed neutral ligand, namely of an imidazole ring. The work group TAMM published constrained geometry complexes with this ligand system for chromium (S. Randoll, P. G. Jones, M. Tamm, *Organometallics* 2008, 27, 3232-3239), for rare earth metals and alkaline earth metals (T. K. Panda, C. G. Hrib, P. G. Jones, J. Jenter, P. W. Roesky, M. Tamm, *Eur. J. Inorg. Chem.* 2008, 4270-4279). Also to be noted in the present context is a further, however, dianionic, CpPN ligand system of the general nomenclature $(Cp^RPRNR)^{2-}$ with a phosphor(III) atom in the bridge by the work group SUNDERMEYER, because the corresponding titanium complexes produce linear, highly molecular polyethylene of high activity (J. Sundermeyer et al. *Eur. J. Inorg. Chem.* 2002, 678-691; *J. Organomet. Chem.* 2001, 640, 21-28).

Further to be noted as known in the art are monoanionic, bidendate phosphoniumdiylide ligands ("CPC," Type A, FIG. 4). Complexes of this flexible chelate-ligand system with metals of the total periodic table have been researched (H. Schmidbaur, *Angew. Chem. Int. Ed.* 1983, 22, 907-927). To be mentioned in this field of interest is primarily the first homoleptic, dissolvent-free organyl complexes of lanthanoids by SCHUMANN. This compound class $[(CPC)_3RE]$ with KZ=6 is sufficiently stabilized by ligands with two α-donors of Type A (FIG. 4) for lutetium and, ranging to the largest of the lanthanoids, lanthanum (H. Schumann, F.-W. Reier, *J. Organomet. Chem.* 1982, 235, 287-294). This is why their characterization and their reactivity were studied. Aside from homoleptic complexes, there are also heteroleptic complexes of rare earths of Type A, which are in most cases stabilized by Cp-co-ligands, and the reactivities of which were studied.

However, not only the classic phosphonium diylides have awakened scientific interest, calling for attention are also a number of phosphor-bridged ansa-metallocene ligands of Type C (CpPCp) with two π-donors in the chelate unit. Complexes of alkali and alkaline earth metals, group 4 metals and iron were prepared with such bis-cyclopentadienyl-phosphonium diylide ligands of Type C. However, not much is known regarding their reactivity. In one example, a CpPCp-iron complex itself serves as catalyst in the polymerization catalysis (H. Schumann, S. Hohmann, *Chemiker-Zeitung* 1976, 100 (7-8), 336).

Although cyclopentadienylidene phosphorane of type $R_3P=C_5R_4$, the structural motif of which is underlying the new ligand class of type B, has been known for a long time as an ampholyte-ionic ligand in the literature, reporting on the advantageous use of complexes containing deprotonated forms of this ligand has been lacking to date (F. Ramirez, S. Levy, *J. Org. Chem.* 1956, 29, 1333).

OBJECTS OF THE INVENTION

Therefore, it is the object of the present invention to provide RE complexes that possess a $C_5R_4$ donor and a C donor, which are bonded via a P-bridge atom in a chelate-like manner to a RE central atom.

SUMMARY OF THE INVENTION

According to the invention, this object is achieved with $\eta^5:\eta^1$-CpPC-CGCs of the general formula 1

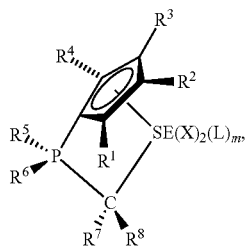
(1)

wherein
RE=Sc, Y, La, Ce, Pr, Nd, Pm, Sm, Eu, Gd, Tb, Dy, Ho, Er, Tm, Yb or Lu;
X=Independently of each other, a monoanionic diorganoamido, bis(trimethylsilyl)amido, halogenide, alkyl, aryl, alkoxo, aryloxo or alkylaluminate ($AlR_4''$) substituent;
L=Neutral ligand, such as triorganylphosphanes ($PR_3$), tertiary amines ($NR_3$), pyridine and/or dissolvent molecule, such as tetrahydrofuran (THF), ether, N,N-dimethylformamide (DMF), dimethylsulfoxide (DMSO), hexamethylphosphoric acid triamide (HMPT), tetrahydropyrane (THP), tetrahydrothiofurane (THT);
R=Alkyl with up to 1-10 carbon atoms or mono- or polycyclic aryl with 6 to 20 carbon atoms;
$R^1$, $R^4$=Independently of each other, H or methyl;
$R^2$, $R^3$: Independently of each other, H or methyl or tertiary butyl, or together a substituted cycloalkyl moiety;
$R^5$, $R^6$=Methyl, n-butyl, tertiary butyl or phenyl;
$R^7$, $R^8$=Independently of each other, H, trimethylsilyl, alkyl with up to 1-10 carbon atoms or mono- or polycyclic aryl with 6 to 20 carbon atoms;
as well as
m=0, 1, 2 or 3.

Alternately, the object according to the invention is achieved with CpPC-CGC of the general formula 2.

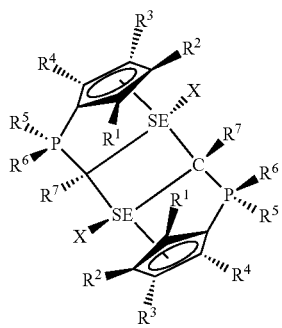
(2)

wherein
RE=Sc, Y, La, Ce, Pr, Nd, Pm, Sm, Eu, Gd, Tb, Dy, Ho, Er, Tm, Yb or Lu;
X=Independently of each other, a monoanionic diorganoamido, bis(trimethylsilyl)amido, halogenido, alkyl, aryl, alkoxo, aryloxo or alkylaluminate ($AlR_4''$) substituent;
R Alkyl with up to 1-10 carbon atoms or mono or polycyclic aryl with 6-20 carbon atoms;
$R^1$,$R^4$=Independently of each other, H or methyl;
$R^2$,$R^3$=Independently of each other, H or methyl or tertiary butyl or together a substituted cycloalkyl moiety;
$R^5$, $R^6$=Methyl, n-butyl, tertiary butyl or phenyl;

R⁷,R⁸=Independently of each other, H, trimethylsilyl, alkyl with up to 1-10 carbon atoms; or mono- or polycyclic aryl with 6-20 carbon atoms.

Preferably, RE=Sc, Y, La, Ce, Nd, Sm or Lu; X=hexamethylene disilazanide, N,N-dimethylbenzylamine (dmba) ortho-metallized, N,N,α-trimethylbenzylamine (tmba) ortho-metallized, a silylmethanide —CH$_2$SiMe$_3$ or —CH(SiMe$_3$)$_2$, benzyl, allyl, Cl, Br or I in the η$^5$:η$^1$-CpPC-CGC.

BRIEF DESCRIPTION OF THE FIGURES

FIG. 1 shows monodentate Cp ligands (left); bidentate ansa-Cp ligands (right) in complexes of rare earth metals.

FIG. 2 shows the first published CGC complex with a CpSiN ligand motif by BERCAW.

FIG. 3 shows CpY-D complexes of rare earth metals and of the metals M (M=Ti, Zr, Hf, Al, V, Cr; X=alkyl, benzyl, amido, halogenide).

FIG. 4 shows analogues of the novel mono-Cp-substituted phosphonium diylide type B in relation to previously known bis-Cp-substituted type A and of the classic type C.

FIG. 5 shows novel RE complexes with: a) monoanionic and b) dianionic CpPC ligand.

FIG. 6 shows $^{13}$C-NMR spectrum of polycaprolactone, polymerized by η$^5$:η$^1$-C$_5$Me$_4$PMe$_2$CH$_2$)La(N(SiMe$_3$)$_2$)$_2$].

DETAILED DESCRIPTION

The (η$^5$:η$^1$-phosphorylide)-rare earth metalloces are preferably selected from the group consisting of:

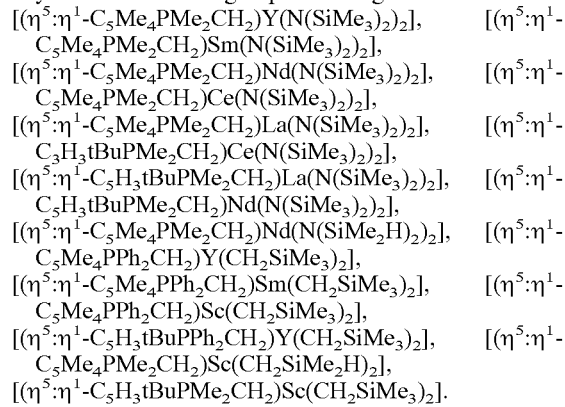

In all complexes, the CpPC unit represents a bidentate, anionic ligand. Particularly preferred was the preparation of complexes with R⁷, R⁸=H, which coordinate with a methylene unit as 6+2 electron donor [R$^{1-4}$$_4$C$_5$—PR$^5$R$^6$—CH$_2$]⁻ on the rare earth metal. The trivalent RE metal atom is additionally coordinated by further anionic ligands X and neutral ligands L. In the special case of R⁸=H, it is possible to further deprotonate the CpPC unit and bond the same as a bidentate, dianionic 6+4 electron ligand [R$^{1-4}$$_4$C$_5$—PR$^5$R$^6$—CR$^7$]$^{2-}$ to the metal atom. However, to be claimed as well shall be such complexes wherein at least one of these ligands bonds in a chelate-like fashion to a bivalent or quadrivalent RE-metal atom (FIG. 5).

The η$^5$:η$^1$-CpPC-CGCes according to the invention are prepared in such a manner that a CH-acidic cyclopentadienylidene phosphorane is reacted with a rare earth metal ligand complex in an aprotic solvent in a temperature range from −20° C. to 120° C. The reaction occurs by way of an elimination of amine, salt or hydrocarbon. Preferably, the reaction is performed in aromatics, hydrocarbons, ethers or in mixtures of these solvents. Particularly preferred is a reaction temperature in the range from −10° C. to 80° C. The CH-acidic cyclopentadienylidene phosphorane is preferably reacted with the rare earth metal ligand complex at a molar ratio between 0.8:1 and 1.2:1. Particularly preferred is the conversion of the CH-acidic cyclopentadienylidene phosphorane with the rare earth metal ligand complex in equimolar quantities.

The η$^5$:η$^1$-CpPC-CGCes according to the invention are used as reagent or catalyst in organic reactions. Further advantageous applications are uses as a catalyst in ring-opening polymerizations for the production of polyesters and as precatalyst in the polymerization of olefins. The use as a precatalyst in the polymerization of conjugated olefins is especially advantageous.

Advantages of metallocene and metallocene-analogous compounds that must be emphasized in a comparison with the heterogeneous ZIEGLER-NATTA catalyst systems are the good solubility in non-polar organic solvents, the well-defined catalytically active location (active side) inside the molecule (single site catalyst) and the stereoselectivity of the C—C-coupling reaction relative to the polymer that can be achieved by the stereochemistry of the catalyst complex (tacticity). Different tacticities of polyolefins result in completely different properties, such as, for example, with regard to the melting point, tensile strength and stability of the polymer, whereby, due to the design of the molecular single-site catalyst, it is possible to adjust the property profile for highly valuable polymers in a targeted fashion. In terms of activity, the new generation of constrained geometry complexes is superior to the metallocenes, allows for a high level of selectivity in the polymerization catalysis and able to withstand considerably higher thermal stresses.

The RE complexes were obtained by reactions of CH-acidic ligand precursors with RE amidene (amine elimination) or with RE alkylene (hydrocarbon elimination). A third method presents the reaction of alkali salts of CpPC ligands with RE halogenides (salt elimination) or an in-situ combination of as RE halogenides with the protonated ligand form [CpPC]H and organolithium compounds or lithium amides as base.

The invention will be illustrated in further detail below based on a number of examples, which are not intended to limit the scope of the invention in any way.

All reactions with substances that react sensitively to hydrolysis and/or oxygen were carried out in heated SCHLENK instruments under a protective argon gas atmosphere. A change tab system with a rotary vane vacuum pump (PFEIFFER, model Duo 010 M, end pressure of ca. 2·10$^{-2}$ bar) was used. The substances were weighed, samples were prepared for analytical studies and substances reacting sensitively to hydrolysis and/or oxygen were stored in a glovebox (Type MB 150 BG-1, BRAUN, Lab Master 130, BRAUN) under a nitrogen atmosphere.

The solvents for reactions that are sensitive to air or moisture were dried according to standard procedures and stored in absorption columns over aluminum oxide/molecular sieve 3 Å/R3-11G catalyst (BASF). The dedeuterized solvents for NMR measurements were also dried according to standard methods and stored over molecular sieve 3 Å.

nBuLi (in hexane), tBuLi (in hexane), MeLi (in Et$_2$O), PhLi (nBu$_2$O) and LiCH$_2$TMS were provided by CHEMETALL. The concentrations of the used solvents of lithium organylene and GRIGNARD reagents were determined by titration with secbutanol vs. 1,10-phenanthroline as indicator.

The NMR spectra were measured on the following instruments at RT:

BRUKER ARX 250: $^1$H (250.1 MHz), $^{13}$C (62.5 MHz)
BRUKER ARX 300: $^1$H (300.1 MHz), $^{13}$C (75.5 MHz), $^{31}$P (121.5 MHz)
BRUKER AMX 300: $^1$H (300.1 MHz), $^{13}$C (75.5 MHz), $^{31}$P (121.5 MHz)
BRUKER DRX 400: $^1$H (400.1 MHz), $^{13}$C (100.6 MHz), $^{31}$P (161.9 MHz), $^7$Li (155.44)
BRUKER DRX 500: $^1$H (500.10 MHz), $^{13}$C (125.8 MHz), $^{31}$P (202.3 MHz), $^{27}$Al (130.3 MHz)

All listed $^{31}$P- and $^{13}$C-NMR spectra are $^1$H-decoupled. The NMR spectra were recorded according to the standard at 298 K, with the exception of the VT-NMR measurements. Residual proton and solvent signals of the corresponding dedeuterized solvents are used for calibrating the $^1$H- and $^{13}$C-NMR spectra.

$^1$H-NMR:
$C_6D_6$: δ=7.16 ppm, $CDCl_3$: δ=7.24 ppm, $d^8$-THF: δ=3.58 ppm, 1.73 ppm, $CD_3CN$: δ=1.94 ppm, $CD_2Cl_2$: δ=5.32 ppm, $d^6$-toluene: δ=7.09 ppm, $d^5$-pyridine: δ=8.71 ppm, $C_6D_5Br$: δ=7.15 ppm, $d^6$-DMSO: δ=2.50 ppm $^{13}$C-NMR:
$C_6D_6$: δ=128.1 ppm, $CDCl_3$: δ=77.0 ppm, $d^8$-THF: δ=49.0 ppm, 24.2 ppm, $CD_3CN$: δ=1.3 ppm, 118.3 ppm, $CD_2Cl_2$: δ=52.79 ppm, $d^6$-toluene: δ=137.5 ppm, $d^5$-pyridine: δ=149.9 ppm, $C_6D_5Br$: δ=131.8 ppm, $d^6$-DMSO: δ=39.5 ppm $^{31}$P-NMR spectra were recorded broadband-decoupled and calibrated externally vs. 85% phosphoric acid or using internal standards ($PPh_3$ in $C_6D_6$: −5.26 ppm).

Couplings between nucleus X and nucleus Y with nuclear spin % via n-bonds are indicated by the coupling constant $^nJ_{xy}$ in Hz.

The following abbreviations were used for the multiplicity of the signals:
s=singlet, d=doublet, t=triplet, q=quadruplet, quin=quintet, m=multiplet.

An exact assignment of the signals was done by 2D NMR spectroscopy (COSY, NOESY, HMQC or HSQC and HMBC NMR spectroscopy). In the NMR analysis, the following numbering was used for the cyclopentadienyl ring:

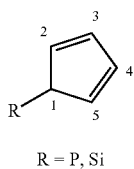

R = P, Si

The infrared spectra were recorded either by a NICOLET 510 M spectrometer (as Nujol rubbings between KBr plates) or an ATR-FT IR spectrometer, model "Alpha-P" by BRUKER (in highly purified material). The absorption bands are indicated in $cm^{-1}$. The characteristics of the absorption bands are captioned by the following abbreviations: w=weak, m=medium, s=strong, $\tilde{v}$=wave number/$cm^{-1}$.

Elemental analyses (C, H, N) were done by the Department for Analytic Chemistry; instrument: CHN-Rapid by HERAEUS. Hydrolysis- and/or oxygen-sensitive substances were weighed in the glove box in a zinc crucible. Information is given in weight %.

The monocrystal x-ray structure analysis was conducted by the Department for Analytical Chemistry of the Philipps-University of Marburg; instrument: IPDS (IPDS-1. STOE). A standard graphite monochromator (Mo-Ka-radiation, (λ=71.073 pm) was used for images. Further information as to crystalline structure analyses can be found in the annex containing crystallographic information. The DIAMOND 3 program was used for the figures containing the molecular structures.

The TGA was done with a TGA/SDTA 851 instrument (by METTLER TOLEDO). For the TGA measurements, the sample was weighed in each time by the ultra-micro scale into a 70 μL aluminum crucible integrated in the instrument. DSC measurements of the polymer samples were taken with a DSC 821e instrument by METTLER TOLEDO. For the DSC measurements, each time, the substance was weighed in into a 40 μL aluminum crucible. A hole was pieced into the lid of the sealed crucible to allow trapped air to escape. A temperature program with two cycles was employed. The samples were measured in a temperature range of −90 to 60° C. at a heating rate of 10 K/min.

The molecular weights could be determined by gel permeation chromatography (GPC) relative to polystryrol as standard in THF at 20° C.

First, it must be noted that the GPC measurement of polyisoprene was taken in pure THF, while, for the measurement of polycaprolactone, trifluoroascetic acid in a concentration of 5% was added to THF as eluent. By adding the acid, it was possible to suppress any possible crystallization of catalyst moieties. Measurements of the same polymers on the same column, however without the addition of acid, did not produce any useful results, which was due to the formation of excess pressure on the column and material. The separation columns for polycaprolactone are two PSS SDV linear columns (10μ, 2×8×600 mm) with a flow rate of 0.8 mL/min. The separation column for the measurements of polyisoprene samples was a PSS SDV linear column (5μ, 30 cm) (+precolumn (SDV precolumn 5 μL)) and a flow rate of 1 mL/min.

Preparation of $[(\eta^5{:}\eta^1{-}C_5R^2{}_3R^1PR^3{}_2CH_2)RE(hmds)_2]$

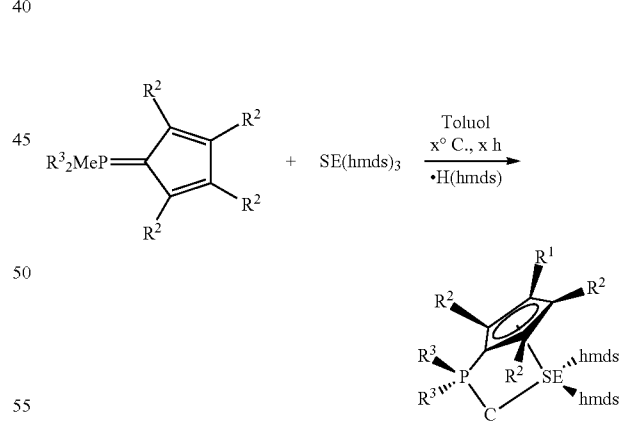

[Toluol = toluene; SE = RE]

General operating procedure: x mmol ligand (1.0 eq) and x mmol RE(hmds)$_3$ (1.0 eq) were first dissolved in x mL toluene. The reaction mixture was stirred for different lengths of time at 80° C., depending on the central atom. A reaction control was done by $^{31}$P-NMR spectroscopy. After the individual reaction time, the solvent and any resulting disilazane [H(hmds)] are removed in vacuo. The residue is suspended in 3-5 mL hexane and made into a paste in an ultrasonic bath, if

EXAMPLE 1

Preparation of [(η⁵:η¹-C₅Me₄PPh₂CH₂)YCl₂]₂

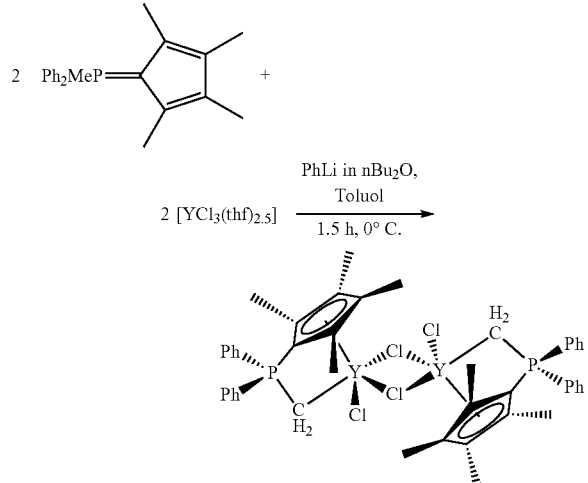

[Toluol = toluene]

97 mg C₅Me₄PPh₂Me (0.30 mmol, 1.00 eq) and 134 mg [YCl₃(THF)₂.₅] (0.357 mmol, 1.18 eq) are provided in 8 mL toluene. The orange-colored solution with light solid was cooled to 0° C., and 0.6 mL of the PhLi solution (0.5 M in nBu₂O/benzene, 0.30 mmol, and 1.00 eq) were dropped in, then the substance then stirred for 1 h at 0° C. During this step, the coloration of the solution disappeared. After the reaction was complete (reaction control by ³¹P-NMR spectroscopy), the reaction mixture was filtered with CELITE and washed twice with 3-4 mL toluene each time. The obtained filtrate was evaporated in a fine vacuum, and the residue was suspended in pentane.

The mixture was then centrifuged, the supernatant solution was discarded and the beige-colored solid material dried in a fine vacuum.

Yield: 129 mg (0.24 mmol, 79%).

The same result is achieved, when the reaction is done in THF as solvent and with the use of [Ycl₃(thp)₂].

EXAMPLE 2

Preparation [η⁵:η¹-C₅Me₄Pme₂CH₂)La(hmds)₂]

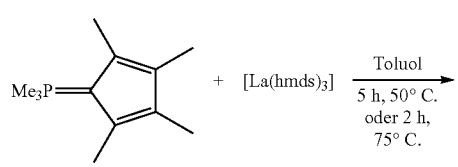

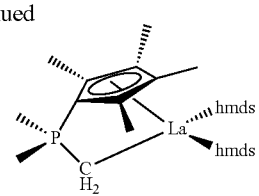

[Toluol = toluene; oder = or]

70 mg C₅Me₄Pme₃ (0.36 mmol, 1.00 eq) and 229 mg [La(hmds)₃] (0.37 mmol, 1.03 eq) are first dissolved in 10 mL toluene. The reaction solution is stirred for 2 h at 75° C. A reaction control is done by ³¹P-NMR spectroscopy. The solvent and H(hmds) are removed at 40° C. in a fine vacuum. The residue is suspended in 3-5 mL hexane and turned into a paste in an ultrasonic bath. The suspension is stored overnight at −30° C. to increase the yield.

Yield: 227 mg (0.35 mmol, 96%); product: colorless solid material.

Monocrystals can be obtained from a hexane solution at −30° C.

EXAMPLE 3

Preparation of [(η⁵:η¹-C₅Me₄PPh₂CH₂)Sm(CH₂SiMe₃)₂] and [(η⁵:η¹-C₅Me₄PPh₂CH)Sm(CH₂SiMe₃)]₂ on NMR Scale

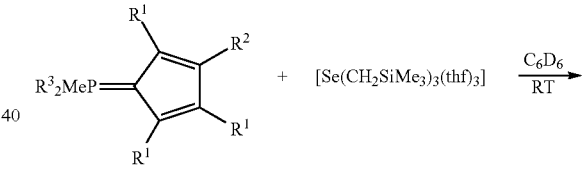

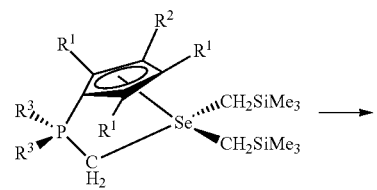

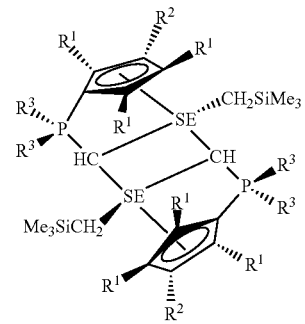

In a small vessel in the glove box, 11.18 mg C$_5$Me$_4$PPh$_2$Me (0.04 mmol, 1.00 eq) are first dissolved in 0.2 mL C$_6$D$_6$. [Sm(CH$_2$SiMe$_3$)$_3$(thf)$_3$] (0.04 mmol, 1.00 eq) is dissolved in 0.2 mL C$_6$D$_6$ in a separate vessel. The ligand solution is slowly dropped in the precursor solution with a syringe, and the reaction vessel is lightly swung back and forth during this step. The reaction mixture is transferred into an NMR tube, rinsed with 0.2 mL C$_6$D$_6$. The compounds are characterized via NMR spectroscopy.

EXAMPLE 4

Preparation of [($\eta^5$:$\eta^1$-C$_5$Me$_4$Pme$_2$CH$_2$)Y(hmds)$_2$]

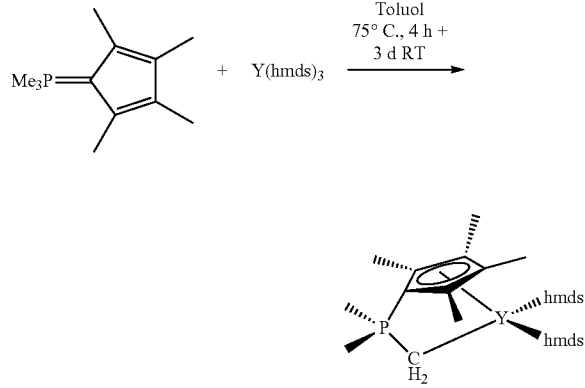

[Toluol = toluene]

Quantity Information:

10 mL toluene, 70 mg Me$_3$PC$_5$Me$_4$ (0.36 mmol, 1.0 eq), 205 mg Y(hmds)$_3$ (0.36 mmol, 1.0 eq); time: 5 h (+3 d); temperature: 50° C. (+3 d, RT)

Yield: 163 mg (0.27 mmol, 75%); color: colorless solid material

Elemental analysis (C$_{24}$H$_{56}$N$_2$Psi$_4$Y, 604.94 g/mol): calculated: C, 47.65; H, 9.33; N, 4.63. found: C, 45.20; H, 8.91; N, 3.77.

$^{31}$P-NMR (121.5 MHz, C$_6$D$_6$): δ/ppm=3.17 (d, $^2J_{P,Y}$=2.08 Hz)

$^1$H-NMR (400.1 MHz, C$_6$D$_6$): δ/ppm=2.04 (s, 6H, C$_5$Me$_4$, 2.5-Cp), 2.00 (s, 6H, C$_5$Me$_4$, 3.4-Cp), 1.13 (d, $^2J_{P,H}$=12.65 Hz, 6H, Pme$_2$), 0.42 (s, 36H, N(SiMe$_3$)$_2$), 0.02 (dd, 2H, $^2J_{P,H}$=9.80 Hz, $^2J_{Y,H}$=2.08 Hz, PCH$_2$Y).

$^{13}$C-NMR (62.8 MHz, C$_6$D$_6$): δ/ppm=125.4 (d, $^{2,3}J_{C,P}$=13.2 Hz), 119.3 (d, $^{2,3}J_{C,P}$=12.1 Hz), 91.2 (d, $^1J_{C,P}$=100.13 Hz, PC$_{Cp}$), 17.4 (d, $^1J_{C,P}$=48.3 Hz, Pme$_2$). 14.9 (s, C$_5$Me$_4$, 3.4-Cp), 12.3 (d, $^3J_{C,P}$=1.44 Hz, C$_5$Me$_4$, 2.5-Cp), 6.62 (s, N(SiMe$_3$)$_2$). The signal for PCH$_2$Y is superimposed by signals EI-MS: m/z (%)=355 (35%), 281 (100%), 254 (48%), 239 (39%), 207 (45%), 123 (100%), 105 (56%), 91 (34%), 77 (27%).

IR (highly purified material): $\tilde{v}$/cm$^{-1}$=2945.47 (m), 2896.22 (m), 1312.51 (m), 1291.25 (m), 1239.93 (s), 1125.00 (w), 951.37 (s), 929.76 (s), 812.79 (s), 770.03 (s), 751.79 (s), 661.53 (m), 607.43 (m), 450.22 (m)

EXAMPLE 5

Preparation of [($\eta^5$:$\eta^1$-C$_5$Me$_4$Pme$_2$CH$_2$)La(hmds)$_2$]

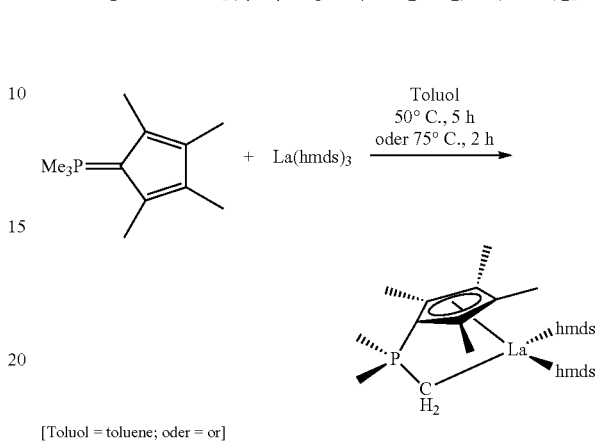

[Toluol = toluene; oder = or]

Quantity Information:

10 mL toluene, 70 mg Me$_3$PC$_5$Me$_4$ (0.36 mmol), 229 mg La(hmds)$_3$ (0.37 mmol, 1.03 eq); time: 2 h (5 h); temperature: 75° C. (50° C.)

Yield: 227 mg (0.35 mmol, 96%); color: colorless solid material

Monocrystals can be obtained from a hexane solution at −30° C.

Elemental analysis (C$_{24}$H$_{56}$N$_2$Psi$_4$La, 654.94 g/mol): calculated: C, 42.29; H, 8.07; N, 4.48. found: C, 38.61; H, 7.73; N, 3.58.

$^1$H-NMR (300.1 MHz, C$_6$D$_6$): δ/ppm=2.08 (s, 6H, C$_5$Me$_4$, 2.5-Cp), 2.04 (s, 6H, C$_5$Me$_4$), 1.13 (d, $^2J_{P,H}$=12.8 Hz, 6H, Pme$_2$), 0.40 (s, 36H, N(SiMe$_3$)$_2$), −0.26 (d, 2H, $^2J_{P,H}$=7.74 Hz, PCH$_2$—La)

$^{13}$C-NMR (75.5 MHz, C$_6$D$_6$): δ/ppm=127.5 (d, $^1J_{P,C}$=57.2 Hz, C$_q$P), 124.28 (s, C$_5$Me$_4$), 120.46 (s, C$_5$Me$_4$, 2.5-Cp), 13.19 (s, C$_5$Me$_4$), 10.70 (s, C$_5$Me$_4$, 2.5-Cp), 17.18 (d, $^1J_{P,C}$=48.0 Hz, Pme$_2$), 4.17 (s, N(SiMe$_3$)$_2$), 1.68 (d, $^1J_{P,C}$=69.9 Hz, PCH$_2$La)

$^{31}$P-NMR (121.5 MHz, C$_6$D$_6$): δ/ppm=4.99
$^{31}$P-NMR (121.5 MHz, Et$_2$O): δ/ppm=6.75

EI-MS: m/z (%)=161 [hmds], 146 [Me$_3$Si—N—SiMe$_2$]

IR (highly purified material): $\tilde{v}$/cm$^{-1}$=2994.48 (m), 2888.58 (w), 1248.65 (m), 1235.29 (m), 1099.08 (w), 1045.19 (w), 1007.16 (s), 892.52 (m), 819.00 (s), 750.03 (w), 743.17 (m), 688.25 (w), 658.17 (s), 597.40 (m), 438.40 (s)

EXAMPLE 6

Preparation of [($\eta^5$:$\eta^1$-C$_3$Me$_4$Pme$_2$CH$_2$)Ce(hmds)$_2$]

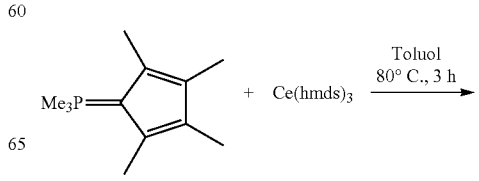

-continued

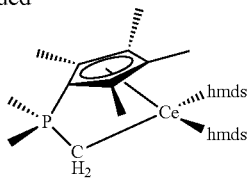

[Toluol = toluene]

Quantity Information:

8 mL toluene, 86 mg Me$_3$PC$_5$Me$_4$ (0.44 mmol, 1.0 eq), 273 mg Ce(hmds)$_3$ (0.44 mmol, 1.0 eq); time: 3 h; temperature: 80° C., the compound is highly sensitive to oxidation.

Yield: 137.5 mg (0.21 mmol, 47.7%); color: light-brown solid material

Monocrystals can be obtained from a hexane solution at −30° C.

Elemental analysis (C$_{24}$H$_{56}$N$_2$Psi$_4$Ce, 656.15 g/mol): calculated: C, 43.93; H, 8.60; N, 4.27. found: C, 28.50; H, 5.26; N, 0.89.

$^1$H-NMR (300.1 MHz, C$_6$D$_6$): δ/ppm=4.36 (s, 6H, C$_5$Me$_4$), 3.70 (s, 6H, C$_5$Me$_4$), 2.38 (bs, 6H, Pme$_2$), 0.13 (s, 36H, N(SiMe$_3$)$_2$), −2.71 (bs, PCH$_2$Ce).

$^{31}$P-NMR (121.5 MHz, C$_6$D$_6$): δ/ppm=−32.3.

$^{13}$C-NMR (75.5 MHz, C$_6$D$_6$): signals disappear in the background noise due to paramagnetism EI-MS: m/z (%)=161 [hmds]*, 146 [Me$_3$Si—N—SiMe$_2$]*

IR (highly purified material): ṽ/cm$^{-1}$=2949.64 (m), 2900.61 (w), 1240.32 (m), 997.91 (m), 967.72 (s), 948.33 (m), 860.47 (m), 825.12 (s), 801.88 (s), 737.84 (s), 660.62 (m), 591.05 (m), 450.45 (w)

EXAMPLE 7

Preparation of [(η$^5$η:η$^1$-C$_5$Me$_4$Pme$_2$CH$_2$)Nd(hmds)$_2$]

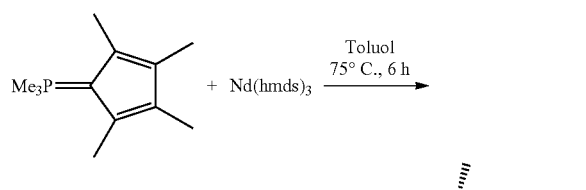

[Toluol = toluene]

Quantity Information:

5 mL toluene, 96 mg Me$_3$PC$_5$Me$_4$ (0.49 mmol, 1.00 eq), 320 mg Nd(hmds)$_3$ (0.51 mmol, 1.04 eq); time: 6 h; temperature: 75° C. (+3 d RT)

Yield: 211.3 mg (0.32 mmol, 65.3%); color: blue solid material

Dark-blue monocrystals could be obtained from a hexane solution at −20° C. after 2 d Elemental analysis: (C$_{24}$H$_{56}$N$_2$Psi$_4$Nd; 657.23 g/mol): calculated: C, 43.66; H, 8.55; N, 4.24. found: C, 39.21; H, 8.08; N, 3.48.

$^{31}$P-NMR (121.5 MHz, C$_6$D$_6$): δ/ppm=−200.7 (bs)

$^1$H-NMR (400.1 MHz, C$_6$D$_6$): δ/ppm=12.88 (s, 6H, C$_5$Me$_4$), 5.16 (s, 6H, C$_5$Me$_4$), −0.75 (bs, 6H, Pme$_2$), −5.10 (bs, 18H, N(SiMe$_3$)$_2$), −7.58 (bs, 18H, N(SiMe$_3$)$_2$), −69.8 or −16.38 (bs, 2H, PCH$_2$Nd)

$^{13}$C-NMR (100.6 MHz, C$_6$D$_6$): δ/ppm=210.2 (s, C$_5$Me$_4$), 180.2 (s, C$_5$Me$_4$), 168.6 (d, $^1$J$_{P,C}$=95.6 Hz, PC$_{Cp}$), 68.3 (bs, C$_5$Me$_4$), 34.0 (d, $^1$J$_{P,C}$=47.3 Hz, Pme$_2$), 24.9 (C$_5$Me$_4$), 6.41 (N(SiMe$_3$)$_2$), 1.18, −13.27 (N(SiMe$_3$)$_2$)

The signal for PCH$_2$Nd could not be identified.

IR (highly purified material): ṽ/cm$^{-1}$=2946.89 (m), 2895.13 (w), 1239.15 (m), 963.29 (s), 945.74 (s), 814.66 (s), 766.15 (s), 747.21 (s), 659.85 (s), 598.84 (s), 438.86 (m)

EXAMPLE 8

Preparation of [(η$^5$:η$^1$-C$_5$Me$_4$Pme$_2$CH$_2$)Sm(hmds)$_2$]

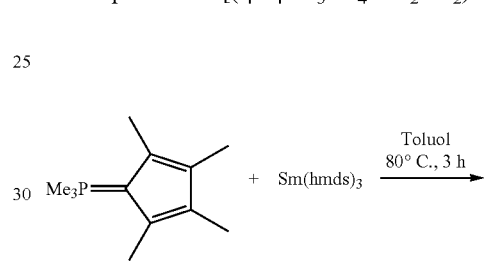

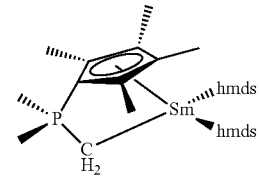

[Toluol = toluene]

Quantity Information:

10 mL toluene, 49 mg Me$_3$PC$_5$Me$_4$ (0.25 mmol, 1.0 eq), 158 mg Sm(hmds)$_3$ (0.25 mmol, 1.0 eq); time: 3 h; temperature: 80° C.

Yield: 98 mg (0.147 mmol, 58.8%); color: beige-colored solid material

Elemental analysis: (C$_{24}$H$_{66}$N$_2$Psi$_4$Sm, 667.25 g/mol): calculated: C, 43.26; H, 8.47; N, 4.20. found: C, 41.73; H, 8.76; N, 3.92.

$^{31}$P-NMR (121.5 MHz, toluene): δ/ppm=37.9 (bs)

$^1$H-NMR (300.1 MHz, C$_6$D$_6$): δ/ppm=3.21 (s, 6H, C$_5$Me$_4$), 2.29 (s, 6H, C$_5$Me$_4$), −0.05 (bs, 6H, Pme$_2$), −1.57 (s, 36H, N(SiMe$_3$)$_2$), −3.86 (bs, 2H, PCH$_2$Sm)

$^{13}$C-NMR (75.5 MHz, C$_6$D$_6$): The signals cannot be identified.

EI-MS: m/z (%)=652.2 [M$^+$-Me].

IR (highly purified material): ṽ/cm$^{-1}$=3067.14 (bm), 2949.59 (w), 1240.45 (m), 998.29 (m), 968.28 (s), 948.34

(m), 860 (m), 825.51 (s), 801.91 (s), 737.98 (s), 660.75 (s), 591.22 (s), 450.30 (m), 405 (m)

EXAMPLE 9

Preparation of [($\eta^5$:$\eta^1$-C$_5$H$_3$tBuPMe$_2$CH$_2$)La(hmds)$_2$]

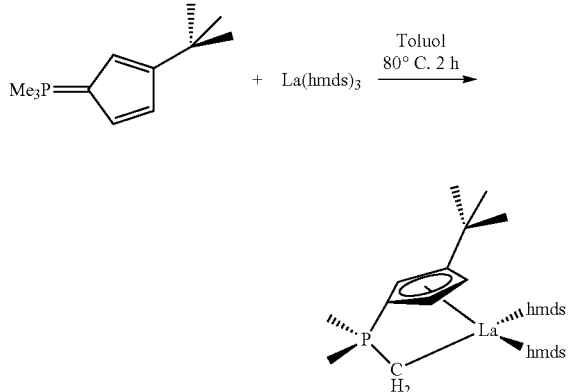

[Toluol = toluene]

Quantity Information:

10 mL toluene, 98.0 mg Me$_3$PC$_5$Me$_4$ (0.50 mmol, 1.00 eq), 415 mg La(hmds)$_3$ (0.67 mmol, 1.34 eq); time: 2 h; temperature: 80° C.

Yield: 194 mg (0.30 mmol, 60%); color: beige-colored solid material Colorless monocrystals could be obtained from a hexane solution at −30° C.

Elemental analysis: (C$_{24}$H$_{56}$PlaN$_2$Si$_4$, 652.0 g/mol): calculated: C, 44.01; H, 8.62; N, 4.28. found: C, 32.17; H, 6.48; N, 1.41.

$^1$H-NMR (C$_6$D$_6$, 400.15 MHz): δ/ppm=6.65 (m, 1H, C$_5$H$_3$), 6.28 (m, 1H, C$_5$H$_3$), 5.91 (m, 1H, C$_5$H$_3$), 1.43 (s, 9H, tBu), 1.08 (d, $^2J_{H,P}$=13.1 Hz, 3H, Pme), 1.03 (d, $^2J_{H,P}$=12.8 Hz, 3H, Pme), 0.45 (bs, 18H, (N(SiMe$_3$)$_2$), 0.33 (s, 18H, (N(SiMe$_3$)$_2$), −0.58 (dd, $^2J_{H,P}$=8.2 Hz, $^2J_{H,H}$=3.6 Hz, 2H, PCH$_2$La)

$^{31}$P-NMR (C$_6$D$_6$, 161.90 MHz): δ/ppm=7.21

$^{13}$C-NMR (75.5 MHz, C$_6$D$_6$): δ/ppm=147.1 (d, $^2J_{CP}$=11.3 Hz, C$_5$H$_3$Bu, C$_4$tBu), 113.8 (d, $^2J_{CP}$=13.6 Hz, C$_5$H$_3$Bu), 112.2 (d, $^2J_{CP}$=12.8 Hz, C$_5$H$_3$tBu), 109.7 (d, $^3J_{CP}$=12.8 Hz, C$_5$H$_3$tBu), 94.3 (d, $^1J_{Cp}$=104.7 Hz, PC$_{CP}$), 33.6 (s, C(CH$_3$)$_3$), 32.4 (d, C(CH$_3$)$_3$), 15.3 (d, $^1J_{CP}$=47.5 Hz, Pme), 12.8 (d, $^1J_{CP}$=53.5 Hz, Pme), 7.95 (d, $^1J_{CP}$=38.42 Hz, PCH$_2$La), 4.4 (bs, (N(SiMe$_3$)$_2$, 24.3 (s, (N(SiMe$_3$)$_2$.

EI-IMS: m/z=196 [Me$_3$PC$_5$H$_3$tBu], 181[Me$_2$PC$_5$H$_3$tBu], 61 [Me$_2$P]

IR (highly purified material): $\tilde{v}$/cm$^{-1}$=3066.61 (w), 2946.81 (m), 2899.33 (w), 1460.77 (w), 1414.74 (m), 1357.36 (w), 1291.67 (s), 1241.43 (s), 1201.91 (s), 1176.04 (s), 1091.89 (s), 1056.23 (m), 1004.24 (s), 975.35 (vs), 747.93 (vs), 9.8067 (w), 861.32 (s), 824.38 (m), 801.99 (m), 765.70 (s), 744.09 (m), 663.42 (vs), 589.99 (vs), 488.12 (w), 449.73 (w)

EXAMPLE 10

Preparation of [($\eta^5$:$\eta^1$-C$_5$H$_3$tBuPMe$_2$CH$_2$)Ce(hmds)$_2$]

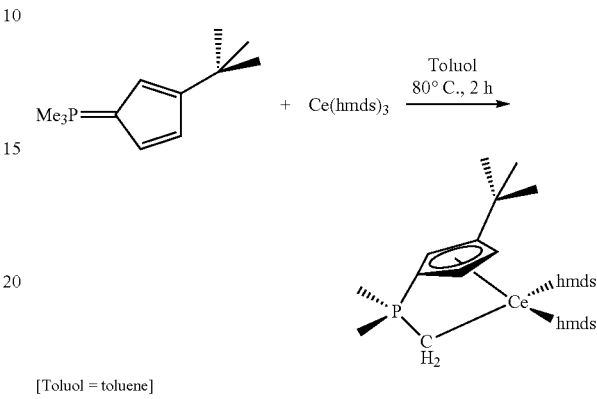

[Toluol = toluene]

Quantity Information:

10 mL toluene, 98.0 mg Me$_3$PC$_5$Me$_4$ (0.51 mmol, 1.00 eq), 380 mg Ce(hmds)$_3$ (0.61 mmol, 1.19 eq); time: 2 h; temperature: 80° C.

Yield: 144 mg (0.22 mmol, 43%); color: brown solid material

Yellow monocrystals could be obtained from a hexane solution at −18° C.

Elemental analysis: (C$_{24}$H$_{56}$PceN$_2$Si$_4$, 653.2 g/mol): calculated: C, 43.93; H, 8.60; N, 4.27. found: C, 39.43; H, 7.97; N, 2.96.

$^1$H-NMR (300.1 MHz, C$_6$D$_6$): δ/ppm=46.27 (s, 1H, C$_5$H$_3$tBu), 18.05 (s, 1H, CH$_3$ tBu), 15.06 (s, 3H), 5.27 (s, 9H, C$_5$H$_3$tBu), −0.81 (very wide signal cannot be integrated N(SiMe$_3$)$_2$), −4.43 (s, 3H), −9.85 (bs, 1H, CH$_3$ tBu), −11.55 (very wide signal cannot be integrated N(SiMe$_3$)$_2$), −25.80 (s, 1H, C$_5$H$_3$tBu), −35.82 (bs, 2H, PCH$_2$Ce). Even after an extended measurement period, it was not possible to obtain useful results from the 2D-spectra of this compound.

$^{31}$P-NMR (121.5 MHz, C$_6$D$_6$): δ/ppm=−27.8 (bs)

EI-MS m/z (%)=181 [Me$_2$P-Cp$^{tBu}$], 196 [Me$_3$P-Cp$^{tBu}$], 61 [Me$_2$P]

IR (highly purified material): $\tilde{v}$/cm$^{-1}$=3065.81 (w), 2946.36 (m), 2897.23 (m), 2858.60 (w), 1427.61 (m), 1355.52 (m), 1291.51 (m), 1200.65 (m), 1174.10 (s), 1091.93 (s), 1057.31 (s), 977.72 (m), 946.70 (vs), 860.54 (m), 825.67 (m), 764.56 (vs), 667.43 (vs), 608.64 (w), 488.04 (w), 450.21 (m)

EXAMPLE 11

Preparation of [($\eta^5$:$\eta^1$-C$_5$H$_3$tBuPMe$_2$CH$_2$)Nd(hmds)$_2$]

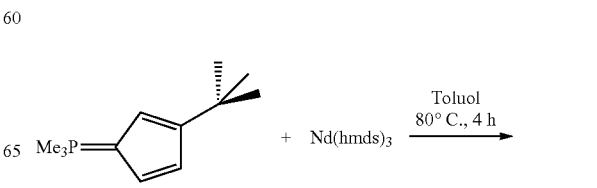

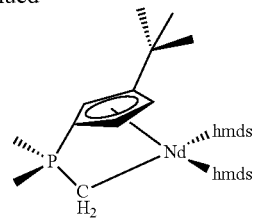

[Toluol = toluene]

Quantity Information:
10 mL toluene, 49 mg Me$_3$PC$_5$Me$_4$ (0.25 mmol, 1.00 eq), 163 mg Nd(hmds)$_3$ (0.26 mmol, 1.04 eq); time: 4 h; temperature: 80° C.

Yield: 118.3 mg (0.18 mmol, 72%); color: blue, crystalline solid material

Elemental analysis (C$_{24}$H$_{56}$N$_2$Psi$_4$Nd, 657.23 g/mol)

$^{31}$P-NMR (121.5 MHz, C$_6$D$_6$) δ/ppm=−178.5.

$^1$H-NMR (300.0 MHz, C$_6$D$_6$) δ/ppm

IR (highly purified material): $\tilde{v}$/cm$^{-1}$=2945.93 (m), 2895.00 (w), 1239.31 (s), 965.02 (s), 945.84 (s), 823.47 (s), 766.02 (m), 746.05 (m), 659.71 (s), 598.92 (s), 440.34 (w)

EXAMPLE 12

Preparation of [(η$^5$:η$^1$-C$_6$H$_3$tBuPPh$_2$CH$_2$)La(hmds)$_2$]

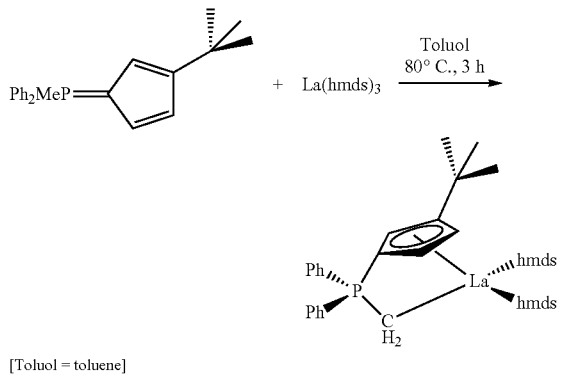

[Toluol = toluene]

Quantity Information:
8 mL toluene, 80 mg C$_5$H$_3$tBuPPh$_2$Me (0.25 mmol, 1.00 eq), 155 mg La(hmds)$_3$ (0.25 mmol, 1.00 eq); time: 3 h; temperature: 80° C.

Yield: 115 mg (0.148 mmol, 59.1%); color: beige-colored solid material

Elemental analysis (C$_{34}$H$_{60}$LaN$_2$PSi$_4$, 778.3 g/mol): calculated: C, 52.42; H, 7.76; N, 3.60.

$^1$H-NMR (C$_6$D$_6$) 400.1 MHz): δ/ppm=7.82-7.74 (m, 4H, Ph$_m$), 7.03-7.00 (m, 6H, Ph$_{o,p}$), 6.77 (m, 1H, C$_5$H$_3$), 6.40 (m, 1H, C$_5$H$_3$), 6.04 (m, 1H, C$_5$H$_3$), 1.39 (s, 9H, tBu), 0.33 (bs, 18H, (N(SiMe$_3$)$_2$), 0.30 (bs, 2H, PCH$_2$La, with superimposed signal for hmds), 0.27 (s, 18H, (N(SiMe$_3$)$_2$)

$^{31}$P-NMR (C$_6$D$_6$, 121.90 MHz): δ/ppm=12.6.

$^{13}$C-NMR (75.5 MHz, C$_6$D$_6$): δ/ppm=132.42 (s, Ph$_p$), 132.41 (s, Ph$_p$), 131.9 (d, $^3J_{C,P}$=2.33 Hz, Ph$_m$), 131.7 (d, $^3J_{C,P}$=2.12 Hz, Ph$_m$), 129.0 (d, $^2J_{C,P}$=5.9 Hz, Ph$_o$), 131.7 (d, $^2J_{C,P}$=5.9 Hz, Ph$_o$), 116.3 (d, $^{2,3}J_{CP}$=13.4 Hz, C$_5$H$_3$tBu), 114.7 (d, $^{2,3}J_{CP}$=13.7 Hz, C$_5$H$_3$tBu), 113.2 (d, $^{2,3}J_{CP}$=13.1 Hz, C$_5$H$_3$tBu), 91.9 (m, PC$_{CP}$), 32.7 (s, C(CH$_3$)$_3$), 4.5 (bs, (N(SiMe$_3$)$_2$) 3.5 (s, (N(SiMe$_3$)$_2$)

The signals of the quaternary carbon atom of the tert-butyl group and the methylene bridge cannot be observed.

IR (highly purified material): $\tilde{v}$/cm$^{-1}$=2949.77 (m), 2900.52 (m), 1240.51 (m), 997.76 (m), 967.78 (s), 948.38 (m), 860.62 (m), 825.20 (s), 801.99 (s), 764.14 (s), 738.03 (m), 660.67 (s), 591.07 (s), 450.52 (m)

EXAMPLE 13

Preparation of [(η$^5$:η$^1$-C$_5$Me$_4$PPh$_2$CH$_2$)LaBr(hmds)(thf)]

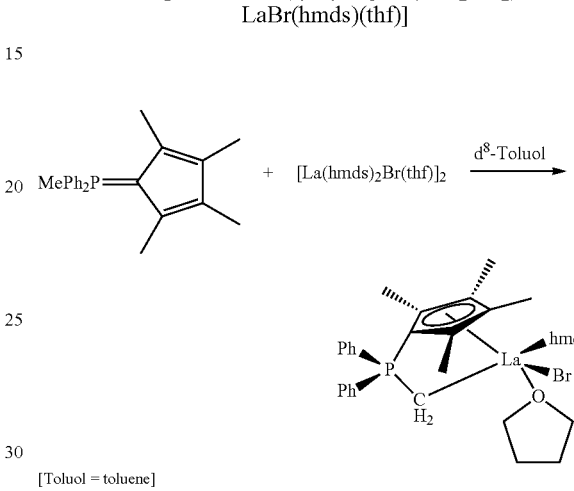

[Toluol = toluene]

16.0 mg (0.044 mmol, 1.05 eq) of C$_5$Me$_4$PPh$_2$CH$_3$ and 25.5 mg (0.042 mmol, 1.00 eq) La(hmds)$_2$Br(thf)]$_2$ were weighed in together into an NMR tube and dissolved in 0.7 mL d$^8$ toluene. The reaction solution is examined by NMR-spectroscopy.

The temperature is then increased by 10° C. and one spectrum each of $^{31}$P-NMR and $^1$H-NMR is measured.

$^{31}$P-NMR (202.3 MHz, d$^8$-tol): δ/ppm=14.4

$^1$H-NMR (500.1 MHz, d$^8$-tol): δ/ppm=7.89-6.99 (m, 10H, Ph), 3.58 (4H, thf), 2.09 (s, 6H, C$_5$Me$_4$), 1.82 (s, 6H, C$_5$Me$_4$), 1.52 (4H, thf), 0.44 (d, 2H, $^2J_{PH}$=6.0 Hz, PCH$_2$La), 0.08 (s, 18H, N(SiMe$_3$)$_2$).

$^{13}$C-NMR (125.8 MHz, d$^8$-tol): δ/ppm=133.1 (Ph), 133.0 (Ph), 131.4 (Ph), 14.1 (C$_6$Me$_4$), 11.9 (C$_6$Me$_4$), 2.66 (s, N(SiMe$_3$)$_2$), 1.39 (PCH$_2$La). The signals for the quaternary carbon atoms of the Cp-ring are not visible. The signal splits of the C atoms of the phenyl ring relative to the phosphor atom cannot be clearly defined due to the width of the signals.

EXAMPLE 14

Preparation of [(η$^5$:η$^1$-C$_5$Me$_4$PMe$_2$CH$_2$)LaBr(hmds)(thf)]

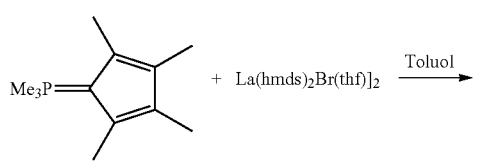

-continued

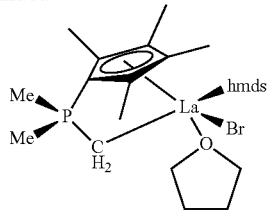

[Toluol = toluene]

5.95 mg (0.030 mmol, 1.00 eq) $C_5Me_4PMe_3$ and 20.61 mg (0.034 mmol, 1.13 eq) $[La(hmds)_2Br(thf)]_2$ are weighed in together into an NMR tube and dissolved in 10 mL toluene. The reaction solution is examined by $^{31}P$-NMR-NMR spectroscopy.

$^{31}P$-NMR (121.5 MHz, $C_6D_6$): δ/ppm=9.15.

$^{1}H$-NMR (300.1 MHz, $C_6D_6$): δ/ppm=3.58 (thf), 2.08 (s, 6H, $C_5Me_4$), 2.04 (s, 6H, $C_5Me_4$), 1.31 (thf), 0.79 (d, 6H, $^{2}J_{P,H}$=12.0 Hz, $PMe_2$), −0.27 (d, 2H, $^{2}J_{P,H}$=9.0 Hz, $PCH_2La$), 0.40 (s, 18H, $N(SiMe_3)_2$).

EXAMPLE 15

Preparation of $[(\eta^5:\eta^1\text{-}C_5Me_4PPh_2CH_2Y(CH_2SiMe_3)_2]$ Via One-Pot Reaction

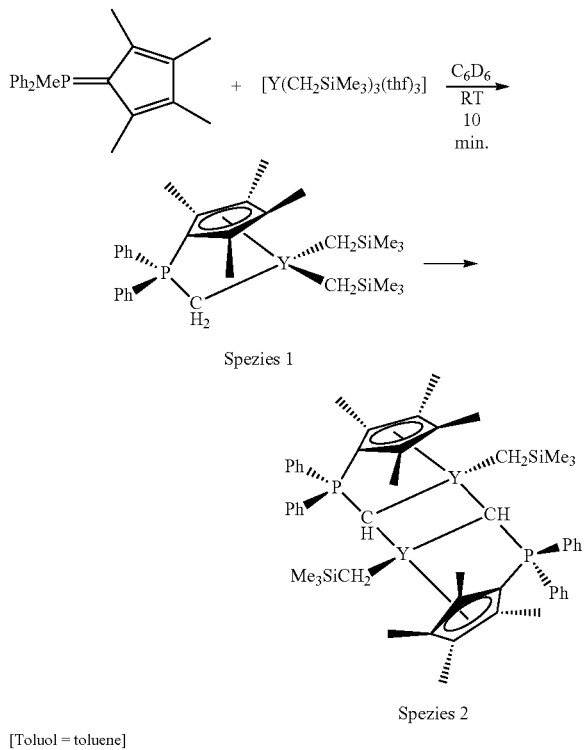

[Toluol = toluene]

99 mg $LiCH_2SiMe_3$ (1.05 mmol, 3.51 eq) is dissolved in 4 mL toluene, cooled to 0° C. and slowly dropped to a suspension, which has also been cooled to 0° C., of 133 mg $[YCl_3thf_{2.5}]$ (0.354 mmol, 1.18 eq) and 96 mg $C_5Me_4PPh_2Me$ (0.300 mmol, 1.00 eq) in 4 mL toluene. A light precipitate fell out of the solution. The mixture is stirred for 1 h at 0° C. A reaction control shows a main product and a secondary product, as well as partially free ligands. The mixture is filtered off in an inverted glass frit, over Celite, and the solvent is removed from the filtrate in vacuo. The residue is then suspended in pentane. After sedimentation of the solid material, the $^{31}P$-NMR spectrum of the supernatant substance shows that both species are now present in the solution in equal ratios. A colorless crystal can be grown from the supernatant solution at −30° C., identifying species 2.

$^{31}P$-NMR (121.5 MHz, toluene): δ/ppm=12.88 (d, $^{1}J_{P,Y}$=5.36 Hz, 86%, species 1), 7.47 (d, $^{1}J_{P,Y}$=5.36 Hz, 9%, species 2), 1.81 (m, 5%, ligand)

$^{31}P$-NWIR (121.5 MHz, pentane): δ/ppm=13.84 (d, $^{1}J_{P,Y}$=5.36 Hz, 33%, species 1), 8.40 (m, 33%, species 2), 2.41 (m, 33%. ligand)

EXAMPLE 16

Ring-Opening Polymerization of ε-Caprolactone with CpPC-bis-hmds Compounds

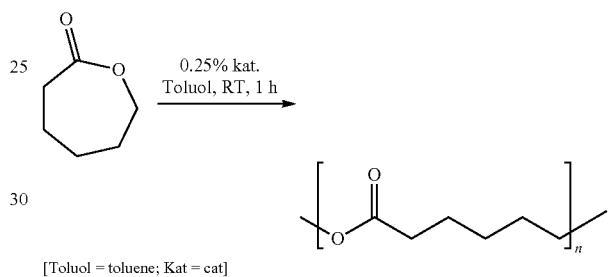

[Toluol = toluene; Kat = cat]

0.25 mmol of the corresponding ligands were is together in 10 mL toluene with 0.25 mmol of the corresponding $RE(hmds)_3$ for a time and temperature as indicated below. The completeness of the conversion of the ligands into a complex is checked by $^{31}P$-NMR spectroscopy. Now, 1 mL (ca. 0.025 mmol complex, 1.00 eq) of the reaction solution is injected in 50 mL toluene and 1.14 g (10 mmol, 400 eq) of ε-caprolactone is added. The substance is stirred for 1 h at RT. Afterwards 900 mL MeOH (mixed in with 0.1 mL $HCl_{concentrate}$) is added to the solution. A white solid material precipitates immediately, and the solution becomes cloudy. The substance is stirred overnight to ensure the completeness of the precipitation. The next day, the polymer is filtered off using a funnel by Büchner and dried for two days at 40° C. in vacuo.

The polymer is dissolved in ca. 50-100 mL $CHCl_3$, filtered with Celite (to separate. $RE_2O_3$, if necessary); the precipitation is repeated in 500 mL MeOH. The polymer is dissolved two more times and re-precipitated to ensure a high level of purity of the material for analytical purposes. The polymer is analyzed by GPC and NMR spectroscopy.

| Catalyst | t/min | Yield | Mw/g/mol | PD |
|---|---|---|---|---|
| $[(\eta^5:\eta^1\text{-}C_5Me_4PMe_2CH_2)Y(N(SiMe_3)_2)_2]$ | 60 | 80% | 204.282 | 2.37 |
| $[(\eta^5:\eta^1\text{-}C_5Me_4PMe_2CH_2)Sm(N(SiMe_3)_2)_2]$ | 60 | 81% | 80.408 | 1.99 |
| $[(\eta^5:\eta^1\text{-}C_5Me_4PMe_2CH_2)Nd(N(SiMe_3)_2)_2]$ | 60 | 60% | 225.549 | 4.13 |
| $[(\eta^5:\eta^1\text{-}C_5Me_4PMe_2CH_2)Ce(N(SiMe_3)_2)_2]$ | 60 | 28% | 86.171 | 2.67 |
| $[(\eta^5:\eta^1\text{-}C_5Me_4PMe_2CH_2)La(N(SiMe_3)_2)_2]$ | 60 | 99% | 255.060 | 1.97 |

-continued

| Catalyst | t/min | Yield | Mw/g/mol | PD |
|---|---|---|---|---|
| [($\eta^5$:$\eta^1$-C$_5$H$_3$tBuPMe$_2$CH$_2$)Ce(N(SiMe$_3$)$_2$)$_2$] | 60 | 78% | 22.00 | 1.57 |
| [($\eta^5$:$\eta^1$-C$_5$H$_3$tBuPMe$_2$CH$_2$)La(N(SiMe$_3$)$_2$)$_2$] | 60 | 45% | 300.380 | 3.55 |
| [($\eta^5$:$\eta^1$-C$_5$H$_3$tBuPMe$_2$CH$_2$)Nd(N(SiMe$_3$)$_2$)$_2$] | 60 | 95% | 213.040 | 1.88 |
| [($\eta^5$:$\eta^1$-C$_5$Me$_4$PMe$_2$CH$_2$)Nd(N(SiMe$_2$)$_2$)$_2$] | 60 | 75% | 189.825 | 2.31 |

Legend: N(SiMe$_3$)$_2$ denotes the anion hmds

There are no signals in the $^{31}$P-NMR spectrum. The signals of the $^{13}$C-NMR spectrum of polycaprolactone in the experiments correspond to those as noted in the literature (FIG. 6).

The detected polydispersities (PD) are in the range of ca. 2. Evidence for a live polymerization is a PD value of 1.0; meaning, all chains are comprised of an equal number of monomer units and therefore evenly grown. However, the initiation rate can naturally be slower than the polymerization rate. This also results in differences as to the chain lengths among chains, which is expressed by a value of PD>1.

EXAMPLE 17

Isoprene Polymerization

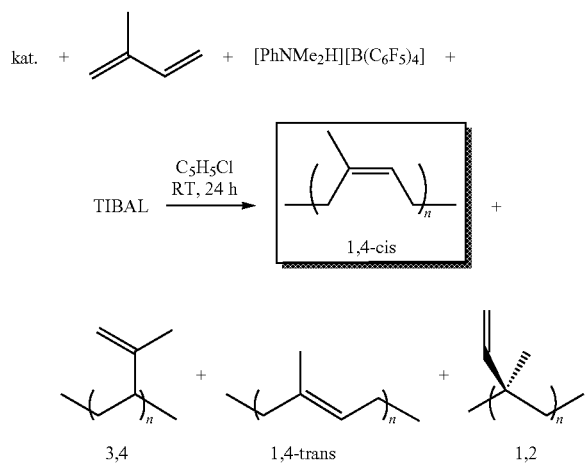

Pre-catalyst synthesis: 0.010 mmol (1.0 eq) of the corresponding ligands in 0.25 mL benzene is dissolved together with 0.011 mmol (1.1 eq) of the corresponding RE(CH$_2$SiMe$_3$)$_3$thf$_x$ in 0.25 mL benzene and added to an NMR tube. The composition of the pre-catalyst is established by $^{31}$P-NMR spectroscopy. Percentage-type information as to the formation of alkyl or the corresponding alkylidene compound is indicated in the table below.

To the solution is now added, inside a schlenk tube, 7.3 mL C$_6$H$_5$Cl until a quantity of 10 mL is reached after all reagents have been added.

1 mL (680 mg) isoprene (10.0 mmol, 1000 eq) is injected, then 1 mL of a (PhNHMe$_2$)[B(C$_6$F$_5$)$_4$] solution in C$_6$H$_5$Cl (8.012 mg/1 mL, 0.01 mmol, 1.0 eq) is injected into the solution. Immediately thereafter, 0.2 mL of a triisobutylaluminum solution in toluene (0.1154 g/mL, 0.116 mmol, 11.6 eq) is added.

The substance is stirred for 24 h at RT.

Afterwards, the viscous solution is added to 100 mL-250 mL HCl-acidic MeOH (0.2 mL HC$_{concentrate}$), with a spatula-tip amount of 2,6-di-tert-butyl-4-methylphenol as stabilizer. A while solid material precipitates immediately, and the solution becomes cloudy. The reaction vessels are rinsed with a few mL of CHCl$_3$; in part, the reaction mixtures have such highly viscosity that it is necessary to rinse several times. The quantity of the added precipitation agent is always ten times the volume relative to the polymer solution. The substance is stirred overnight to ensure a complete precipitation. On the following day, polyisoprene is filtered off using a BUCHNER funnel and dried at RT in vacuo for three days.

The polymer is dissolved in ca. 10 mL-50 mL CHCl$_3$, filtered through a syringe filter (to separate any possible RE$_2$O$_3$ or other contaminations), then precipitated again in 100 mL-250 mL MeOH to ensure a high level of purity for analytical purposes.

The polymer is analyzed by GPC, TGA, DSC and NMR spectroscopy.

Table: The $^{31}$P-NMR spectroscopic control shows the ratio of the RE alkyl relative to the RE alkylidene compound immediately after adding the reactants in benzene [(C$_5$R$^1$R$^2$$_3$PR$^3$$_2$CH$_2$)RE(CH$_2$SiMe$_3$)$_2$]$_2$ (R$^1$=tBu, Me; R$^2$=H, Me; R$^3$=Me, Ph).

Reactants

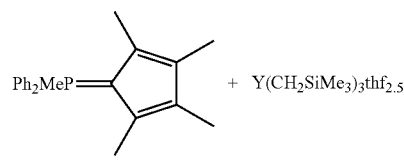

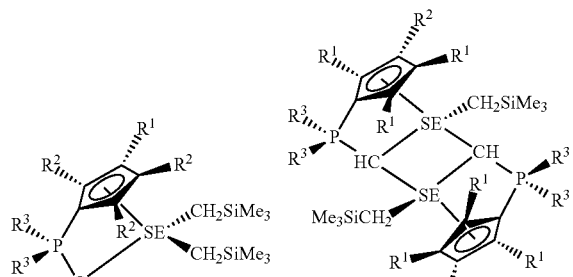

90%          10%

-continued

| Reactants | [structure 1] | [structure 2] |
|---|---|---|
| Ph₂MeP=C₅Me₄ + Sm(CH₂SiMe₃)₃thf₃ | 38% | 62% |
| Ph₂MeP=C₅Me₄ + Sc(CH₂SiMe₃)₃thf₂ | 100% | — |
| Ph₂MeP=C₅H₃tBu + Y(CH₂SiMe₃)₃thf₂.₅ | 95% | 5% |
| Ph₂MeP=C₅H₃tBu + Sc(CH₂SiMe₃)₃thf₂ | 100% | — |
| Me₃P=C₅H₃tBu + Sc(CH₂SiMe₃)₃thf₂ | 100% | — |
| Me₃P=C₅Me₄ + Sc(CH₂SiMe₃)₃thf₂ | 100% | — |

TABLE

Isomers polyisoprene, identified by ¹H-NMR spectroscopy

| Precatalyst | Yield | cis/% | 3.4/% | trans/% | 1.2/% |
|---|---|---|---|---|---|
| [(η⁵:η¹-C₅Me₄PPh₂CH₂)Y(CH₂SiMe₃)₂] | 100% | 57.3 | 20.7 | 22.0 | — |
| [(η⁵:η¹-C₅Me₄PPh₂CH₂)Sm(CH₂SiMe₃)₂] | 100% | 16.4 | 83.6 | — | — |
| [(η⁵:η¹-C₅Me₄PPh₂CH₂)Sc(CH₂SiMe₃)₂] | 96.3% | 80.5 | 19.5 | — | — |
| [(η⁵:η¹-C₅H₃tBuPPh₂CH₂)Y(CH₂SiMe₃)₂] | 5.9% | 52.4 | 25.9 | 21.7 | — |
| [(η⁵:η¹-C₅H₃tBuPPh₂CH₂)Sc(CH₂SiMe₃)₂] | 13.2% | 80.0 | 12.1 | 7.9 | — |
| [(η⁵:η¹-C₅H₃tBuMe₂CH₂)Sc(CH₂SiMe₃)₂] | 100% | 82.2 | 17.8 | — | — |
| [(η⁵:η¹-C₅Me₄PMe₂CH₂)Sc(CH₂SiMe₂H)₂] | 4.1% | 28.6 | 30.9 | 40.5 | — |
| [Sc(CH₂SiMe₃)₃thf₂] | 100% | 60.5 | 20.7 | 18.8 | — |
| [Y(CH₂SiMe₃)₃thf₂] | 100% | 61.4 | 19.5 | 19.1 | — |
| [Sm(CH₂SiMe₃)₃thf₂] | 100% | 70.3 | 16.3 | 13.4 | — |

TABLE-continued

Isomers polyisoprene, identified by $^1$H-NMR spectroscopy

| Precatalyst | Yield | cis/% 3.4/% trans/% 1.2/% |
|---|---|---|
| [($\eta^5$: $\eta^1$-C$_5$Me$_4$PPh$_2$CH$_2$)Sc(CH$_2$SiMe$_3$)$_2$], without borate, without TIBAL | 0% | |

TABLE 10

Glass transition temperature, established by TLC measurement

| Precatalyst | Glass transition |
|---|---|
| [($\eta^5$: $\eta^1$-C$_5$Me$_4$PPh$_2$CH$_2$)Y(CH$_2$SiMe$_3$)$_2$] | −51.1° C. |
| [($\eta^5$: $\eta^1$-C$_5$Me$_4$PPh$_2$CH$_2$)Sm(CH$_2$SiMe$_3$)$_2$] | 6.3° C. |
| [($\eta^5$: $\eta^1$-C$_5$Me$_4$PPh$_2$CH$_2$)Sc(CH$_2$SiMe$_3$)$_2$] | −50.83 |
| [($\eta^5$: $\eta^1$-C$_5$H$_3$tBuPPh$_2$CH$_2$)Y(CH$_2$SiMe$_3$)$_2$] | Not determined |
| [($\eta^5$: $\eta^1$-C$_5$H$_3$tBuPPh$_2$CH$_2$)Sc(CH$_2$SiMe$_3$)$_2$] | −57.6° C. |
| [($\eta^5$: $\eta^1$-C$_5$H$_3$tBuMe$_2$CH$_2$)Sc(CH$_2$SiMe$_3$)$_2$] | −52.7° C. |
| [($\eta^5$: $\eta^1$-C$_5$Me$_4$PMe$_2$CH$_2$)Sc(CH$_2$SiMe$_2$H)$_2$] | Not determined |
| [Sc(CH$_2$SiMe$_3$)$_3$thf$_2$] | −51.3° C. |
| [Y(CH$_2$SiMe$_3$)$_3$thf$_2$] | −53.5° C. |
| [Sm(CH$_2$SiMe$_3$)$_3$thf$_2$] | −56.0° C. |
| Natural rubber | −68° C. |

*not determined since no substance was available any longer. Yield <6%

It could be determined by TGA measurements that there is no significant break-down in excess of 5% until the degradation point at ca. 390-450° C. is reached. TLC measurements show that the polymer has, with a glass point of ca. −50° C. and without melting point, ideal properties that are typical for an elastomer until the degradation point is reached.

TABLE

Polydispersity and molecular weights, detected by GPC

| Precatalyst | Mw/g/mol | PD |
|---|---|---|
| [($\eta^5$: $\eta^1$-C$_5$Me$_4$PPh$_2$CH$_2$)Y(CH$_2$SiMe$_3$)$_2$]* | >600.000 | |
| [($\eta^5$: $\eta^1$-C$_5$Me$_4$PPh$_2$CH$_2$)Sm(CH$_2$SiMe$_3$)$_2$]** | Not detectable | |
| [($\eta^5$: $\eta^1$-C$_5$Me$_4$PPh$_2$CH$_2$)Sc(CH$_2$SiMe$_3$)$_2$]* | >600.000 | |
| [($\eta^5$: $\eta^1$-C$_5$H$_3$tBuPPh$_2$CH$_2$)Y(CH$_2$SiMe$_3$)$_2$] | 70.3970 | 2.591 |
| [($\eta^5$: $\eta^1$-C$_5$H$_3$tBuPPh$_2$CH$_2$)Sc(CH$_2$SiMe$_3$)$_2$]* | >600.000 | |
| [($\eta^5$: $\eta^1$-C$_5$H$_3$tBuPMe$_2$CH$_2$)Sc(CH$_2$SiMe$_3$)$_2$]** | Not detectable | |
| [($\eta^5$: $\eta^1$-C$_5$Me$_4$PMe$_2$CH$_2$)Sc(CH$_2$SiMe$_2$H)$_2$]** | Not detectable | |
| [Sc(CH$_2$SiMe$_3$)$_3$thf$_2$]*** | ca. 60.000 | |
| [Y(CH$_2$SiMe$_3$)$_3$thf$_2$]*** | ca. 75.000 | |
| [Sm(CH$_2$SiMe$_3$)$_3$thf$_2$] | 367.700 | 3.099 |
| Natural rubber | 2-4 × 10$^6$ | 3-10 |

*Molecular weight so great that it ends up as void volume (>10), the molecular weight (Mw) cannot be detected exactly.
**Samples are poorly soluble in THF, and/or they cannot be completely pressed through the syringe filter.
***Curve with more than one maximum, bimodal distribution The detected polydispersities (PD) are also in a range around 2. In this case as well, the catalysts start the polymerization so fast that the polymerization rate is greater than the initiation rate. Moreover, the chains are extraordinarily long, such that any measurement that yields an exact value Mw/g/mol is not possible. Without determining the Mw, it is not possible to detect polydispersities, which are, however, not important in the synthesis of natural rubber (natural rubber: PD 3-10).

It is claimed:

1. $\eta^5$:$\eta^1$-cyclopentadienylidene-phosphorane constrained geometry complexes of rare earth metals ($\eta^5$:$\eta^1$-CpPC-CGC) of formula 1:

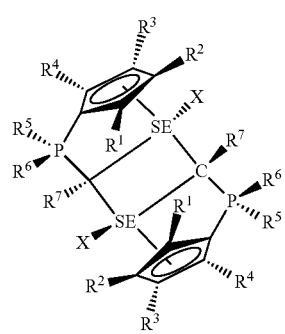

(1)

wherein SE is Sc, Y, La, Ce, Pr, Nd, Pm, Sm, Eu, Gd, Tb, Dy, Ho, Er, Tm, Yb or Lu;
X is independently of each other, a monoanionic diorganoamido, bis(trimethylsilyl)amido, halogenido, alkyl, aryl, alkoxo, aryloxo or alkylaluminate (AlR$_4$") substituent;
L is neutral ligand and/or dissolvent molecule;
R$^1$ and R$^4$ is independently of each other, H or methyl;
R$^2$ and R$^3$ are independently of each other, H or methyl or tert-butyl or together a substituted cycloalkyl moiety;
methyl, n-butyl, tort-butyl or phenyl;
R$^5$ and R$^6$ are independently of each other, H, trimethylsilyl, alkyl with 1-10 carbon atoms;
R$^7$ and R$^8$ are atoms or mono- or polycyclic aryl with 6-20 carbon atoms; and m is 0, 1, 2 or 3.

2. $\eta^5$:$\eta^1$-cyclopentadienylidene-phosphorane constrained geometry complexes of rare earth metals ($\eta^5$:$\eta^1$-CpPC-CGC) of formula 2:

(2)

wherein SE is Sc, Y, La, Ce, Pr, Nd, Pm, Sm, Eu, Gd, Tb, Dy, Ho, Er, Tm, Yb or Lu;
X is independently of each other, a monoanionic diorganoamido, Bis(trimethylsilyl)amido, halogenido, alkyl, aryl, alkoxo, aryloxo or alkylaluminate (AlR$_4$") substituent;
L neutral ligand and/or dissolvent molecule;
R$^1$ and R$^4$ are independently of each other, H or methyl;
R$^2$ and R$^3$ are independently of each other, H or methyl or tert-butyl or together a substituted cycloalkyl moiety;

$R^5$ and $R^6$ are methyl, n-butyl, tert-butyl or phenyl;

$R^7$ and $R^8$ are independently of each other, H, trimethylsilyl, alkyl with 1-10 carbon atoms or mono- or polycyclic aryl with 6-20 carbon atoms.

3. $\eta^5$:$\eta^1$-CpPC-CGC according to claim 1, wherein SE is Sc, Y, La, Ce, Nd, Sm or Lu.

4. $\eta^5$:$\eta^1$-CpPC-CGC according to claim 2, wherein SE is Sc, Y, La, Ce, Nd, Sm or Lu.

5. $\eta^5$:$\eta^1$-CpPC-CGC according to claim 1, wherein
X is hexamethylenedisilazanide, N, N-dimethylbenzylamine ortho-metallized, or N,N,α-trimethylbenzylamine ortho-metallized.

6. $\eta^5$:$\eta^1$-CpPC-CGC according to claim 2, wherein
X is hexamethylenedisilazanide, N,N-dimethylbenzylamine ortho-metallized, N,N, or α-trimethylbenzylamine ortho-metallized.

7. $\eta^5$:$\eta^1$-CpPC-CGC according to claim 1, wherein the neutral ligand is $PR_3$, $NR_3$, pyridine, wherein R is an alkyl with up to 1-10 carbon atoms or a mono- or polycyclic aryl with 6 to 20 carbon atoms, and the dissolvent molecule is THF, ether, DMF, DMSO, HMPT, tetrahydropyran or tetrahydrothiofuran.

8. $\eta^5$:$\eta^1$-CpPC-CGC according to claim 2, wherein the neutral ligand is $PR_3$, $NR_3$, pyridine, wherein R is an alkyl with up to 1-10 carbon atoms or a mono- or polycyclic aryl with 6 to 20 carbon atoms, and the dissolvent molecule is THF, ether, DMF, DMSO, HMPT, tetrahydropyran or tetrahydrothiofuran.

9. $\eta^5$:$\eta^1$-CpPC-CGC selected from the group consisting of:

[($\eta^5$:$\eta^1$-$C_5Me_4PMe_2CH_2$)Y(N(SiMe$_3$)$_2$)$_2$],
[($\eta^5$:$\eta^1$-$C_5Me_4PMe_2CH_2$)Sm(N(SiMe$_3$)$_2$)$_2$],
[($\eta^5$:$\eta^1$-$C_5Me_4PMe_2CH_2$)Nd(N(SiMe$_3$)$_2$)$_2$],
[($\eta^5$:$\eta^1$-$C_5Me_4PMe_2CH_2$)Ce(N(SiMe$_3$)$_2$)$_2$],
[($\eta^5$:$\eta^1$-$C_5Me_4PMe_2CH_2$)La(N(SiMe$_3$)$_2$)$_2$],
[($\eta^5$:$\eta^1$-$C_5H_3tBuPMe_2CH_2$)Ce(N(SiMe$_3$)$_2$)$_2$],
[($\eta^5$:$\eta^1$-$C_5H_3tBuPMe_2CH_2$)La(N(SiMe$_3$)$_2$)$_2$],
[($\eta^5$:$\eta^1$-$C_5H_3tBuPMe_2CH_2$)Nd(N(SiMe$_3$)$_2$)$_2$],
[($\eta^5$:$\eta^1$-$C_5Me_4PMe_2CH_2$)Nd(N(SiMe$_2$H)$_2$)$_2$],
[($\eta^5$:$\eta^1$-$C_5Me_4PPh_2CH_2$)Y(CH$_2$SiMe$_3$)$_2$],
[($\eta^5$:$\eta^1$-$C_5Me_4PPh_2CH_2$)Sm(CH$_2$SiMe$_3$)$_2$],
[($\eta^5$:$\eta^1$-$C_5Me_4PPh_2CH_2$)Sc(CH$_2$SiMe$_3$)$_2$],
[($\eta^5$:$\eta^1$-$C_5H_3tBuPPh_2CH_2$)Y(CH$_2$SiMe$_3$)$_2$],
[($\eta^5$:$\eta^1$-$C_5Me_4PMe_2CH_2$)Sc(CH$_2$SiMe$_2$H)$_2$], and
[($\eta^5$:$\eta^1$-$C_5H_3tBuPMe_2CH_2$)Sc(CH$_2$SiMe$_3$)$_2$].

10. A method of producing the $\eta^5$:$\eta^1$-CpPC-CGC according to claim 1, wherein a CH-acidic cyclopentadienylidenephosphorane is reacted with a rare earth metal ligand complex in an aprotic solvent in the temperature range of −20° C. to 120° C.

11. A method of producing the $\eta^5$:$\eta^1$-CpPC-CGC according to claim 2, wherein a CH-acidic cyclopentadienylidenephosphorane is reacted with a rare earth metal ligand complex in an aprotic solvent in the temperature range of −20° C. to 120° C.

12. The method according to claim 10, wherein the method is achieved by way of an amine elimination, salt elimination or hydrocarbon elimination.

13. The method according to claim 11, wherein the method is achieved by way of an amine elimination, salt elimination or hydrocarbon elimination.

14. The method according to claim 10, wherein the method is achieved in aromatics, hydrocarbons or ethers or in mixtures of these solvents.

15. The method according to claim 11, wherein the method is achieved in aromatics, hydrocarbons or ethers or in mixtures of these solvents.

16. The method according to claim 10, wherein the CH-acidic cyclopentadienylidenephosphorane is reacted with the rare earth metal ligand complex at a molar ratio of 0.8:1 to 1.2:1.

17. The method according to claim 11, wherein the CH-acidic cyclopentadienylidenephosphorane is reacted with the rare earth metal ligand complex at a molar ratio of 0.8:1 to 1.2:1.

18. The method according to claim 10, wherein the CH-acidic cyclopentadienylidenephosphorane is reacted with a rare earth metal ligand complex in equimolar quantities.

19. The method according to claim 11, wherein the CH-acidic cyclopentadienylidenephosphorane is reacted with a rare earth metal ligand complex in equimolar quantities.

20. A method of performing an organic reaction wherein of $\eta^5$:$\eta^1$-CpPC-CGC according to claim 1 is present as reagent or catalyst.

21. A method of performing an organic reaction wherein of $\eta^5$:$\eta^1$-CpPC-CGC according to claim 2 is present as reagent or catalyst.

22. The method according to claim 20 wherein the $\eta^5$:$\eta^1$-CpPC-CGC is a catalyst for ring-opening polymerization reactions in the production of polyesters.

23. The method according to claim 21 wherein the $\eta^5$:$\eta^1$-CpPC-CGC is a catalyst for ring-opening polymerization reactions in the production of polyesters.

24. A method of performing an organic reaction wherein of $\eta^5$:$\eta^1$-CpPC-CGC according to claim 1 is present as a precatalyst and the organic reaction is polymerization of olefins.

25. A method of performing an organic reaction wherein of $\eta^5$:$\eta^1$-CpPC-CGC according to claim 2 is present as a precatalyst and the organic reaction is polymerization of olefins.

* * * * *